US012415999B2

(12) United States Patent
Callahan et al.

(10) Patent No.: US 12,415,999 B2
(45) **Date of Patent: *Sep. 16, 2025**

(54) NUCLEIC ACID ISOLATION AND INHIBITOR REMOVAL FROM COMPLEX SAMPLES

(71) Applicant: QIAGEN SCIENCES LLC, Germantown, MD (US)

(72) Inventors: Heather Callahan, Escondido, CA (US); Victoria Nieciecki, Vista, CA (US); Emelia Deforce, Oceanside, CA (US); Eddie W. Adams, San Diego, CA (US)

(73) Assignee: QIAGEN Sciences, LLC, Germantown, MD (US)

( * ) Notice: Subject to any disclaimer, the term of this patent is extended or adjusted under 35 U.S.C. 154(b) by 736 days.

This patent is subject to a terminal disclaimer.

(21) Appl. No.: 17/049,742

(22) PCT Filed: Apr. 17, 2019

(86) PCT No.: PCT/US2019/027966

§ 371 (c)(1),
(2) Date: Oct. 22, 2020

(87) PCT Pub. No.: WO2019/209597

PCT Pub. Date: Oct. 31, 2019

(65) Prior Publication Data

US 2023/0159911 A1 May 25, 2023

Related U.S. Application Data

(60) Provisional application No. 62/662,063, filed on Apr. 24, 2018.

(51) Int. Cl.
*C12N 15/10* (2006.01)
*C12Q 1/6806* (2018.01)

(52) U.S. Cl.
CPC ..... *C12N 15/1003* (2013.01); *C12N 15/1006* (2013.01); *C12Q 1/6806* (2013.01)

(58) Field of Classification Search
CPC .................................................. C12N 15/1003
See application file for complete search history.

(56) References Cited

U.S. PATENT DOCUMENTS

| | | | |
|---|---|---|---|
| 4,748,234 | A | 5/1988 | Dorin et al. |
| 4,843,155 | A | 6/1989 | Chomczynski |
| 5,081,010 | A | 1/1992 | Cummins et al. |
| 5,342,931 | A | 8/1994 | Woodard et al. |
| 5,391,497 | A | 2/1995 | Menon et al. |
| 5,637,687 | A | 6/1997 | Wiggins |
| 5,648,225 | A | 7/1997 | Kim et al. |
| 5,665,359 | A | 9/1997 | Ho et al. |
| 5,705,628 | A | 1/1998 | Hawkins |
| 5,777,098 | A | 7/1998 | Gray et al. |
| 5,834,282 | A | 11/1998 | Habuchi et al. |
| 5,898,071 | A | 4/1999 | Hawkins |
| 5,922,328 | A | 7/1999 | Spector et al. |
| 6,534,262 | B1 | 3/2003 | McKernan et al. |
| 6,579,697 | B1 | 6/2003 | Wallach et al. |
| 6,599,496 | B2 | 7/2003 | Carter et al. |
| 7,074,916 | B2 | 7/2006 | Bastian et al. |
| 7,429,648 | B1 | 9/2008 | Wallach et al. |
| 7,459,548 | B2 | 12/2008 | Brolaski et al. |
| 8,399,218 | B2 | 3/2013 | Gupta et al. |
| 8,834,694 | B2 | 9/2014 | Brolaski et al. |
| 8,889,393 | B2 | 11/2014 | Sjöblom et al. |
| 9,051,563 | B2 | 6/2015 | Forman et al. |
| 2003/0153083 | A1 | 8/2003 | Shir et al. |
| 2005/0059021 | A1 | 3/2005 | Farid et al. |
| 2005/0060761 | A1 | 3/2005 | Vazquez-Martinez et al. |

(Continued)

FOREIGN PATENT DOCUMENTS

| | | | |
|---|---|---|---|
| CA | 772145 | A | 11/1967 |
| CN | 101563063 | A | 10/2009 |

(Continued)

OTHER PUBLICATIONS

Mustafa et al., "Removal of humic acid from peat soils by using AlCl3 prior to DNA extraction" AIP Conference Proceedings 1844, 030007 doi: 10.1063/1.4983434 (Year: 2017).*
Dong et al., "Removal of humic substances from soil DNA using aluminium sulfate" Journal of Microbiological Methods Journal of Microbiological Methods vol. 66 pp. 217-222 doi:10.1016/j.mimet.2005.11.010 (Year: 2006).*
Braid et al., "Removal of PCR inhibitors from soil DNA by chemical flocculation" Journal of Microbiological Methods vol. 52 pp. 389-393 (Year: 2003).*
Serres et al., "A functional update of the *Escherichia coli* K-12 genome," *Genome Biology* 2(9):research0035.1-0035.7, 7 Pages (2001).
WiseGEEK, "How Many Species of Bacteria Are There?" http://wisegeek.com/how-many-species-of-bacteria-are-there.htm, 2 pages, Sep. 23, 2011.

(Continued)

*Primary Examiner* — Eric Olson
(74) *Attorney, Agent, or Firm* — Seed Intellectual Property Law Group LLP

(57) ABSTRACT

The present disclosure provides methods for isolating nucleic acids from a sample, comprising: (a) contacting a sample, a lysate of the sample, a supernatant of the lysate, or a portion of the sample, the lysate or the supernatant with one or more first agents (e.g., protein precipitating agents) and one or more second agents (e.g., inhibitor removing agents) to generate a mixture, (b) separating the mixture of step (a) into a solid phase and a liquid phase, wherein the one or more second agents are primarily in the solid phase, and (c) isolating nucleic acids from the liquid phase of step (b). Compositions and kits useful in such methods are also disclosed. Further disclosed are methods, compositions and kits for preparing a lysate using a lytic reagent comprising one or more relatively mild chaotropic agents and one or more phosphates from a sample, especially a complex sample, such as a soil or stool sample.

36 Claims, 9 Drawing Sheets

(56) References Cited

U.S. PATENT DOCUMENTS

| | | | | |
|---|---|---|---|---|
| 2005/0282202 | A1* | 12/2005 | Brolaski | C12N 15/1003 435/270 |
| 2007/0190535 | A1 | 8/2007 | Hall, Jr. et al. | |
| 2007/0202511 | A1 | 8/2007 | Chen et al. | |
| 2008/0038753 | A1 | 2/2008 | Branum et al. | |
| 2008/0146641 | A1 | 6/2008 | Urano et al. | |
| 2008/0152608 | A1 | 6/2008 | Cropper et al. | |
| 2009/0048437 | A1 | 2/2009 | Lee et al. | |
| 2009/0111159 | A1 | 4/2009 | Brolaski et al. | |
| 2010/0093634 | A1 | 4/2010 | Welling et al. | |
| 2010/0292316 | A1 | 11/2010 | Sanders et al. | |
| 2010/0331534 | A1 | 12/2010 | Khan et al. | |
| 2012/0178091 | A1 | 7/2012 | Glezer et al. | |
| 2012/0271042 | A1 | 10/2012 | Jiang et al. | |
| 2013/0041145 | A1* | 2/2013 | Kirsch | C12N 15/1003 435/219 |
| 2013/0164819 | A1 | 6/2013 | Sjöblom et al. | |
| 2014/0051844 | A1 | 2/2014 | Forman et al. | |
| 2014/0212868 | A1 | 7/2014 | Wilmes et al. | |
| 2014/0288272 | A1 | 9/2014 | Allison et al. | |
| 2015/0185126 | A1 | 7/2015 | Callahan et al. | |
| 2017/0021333 | A1 | 1/2017 | Kovacs et al. | |
| 2018/0245064 | A1 | 8/2018 | Moroney et al. | |
| 2019/0071665 | A1 | 3/2019 | Callahan et al. | |
| 2021/0238580 | A1* | 8/2021 | O'Neil | G01N 1/286 |
| 2021/0246160 | A1* | 8/2021 | Callahan | C07K 1/14 |
| 2021/0292742 | A1* | 9/2021 | O'Neil | C12Q 1/6806 |

FOREIGN PATENT DOCUMENTS

| | | | | |
|---|---|---|---|---|
| CN | 104152436 | A | 11/2014 | |
| EP | 2 199 295 | A1 | 6/2010 | |
| EP | 2 345 719 | A1 | 7/2011 | |
| EP | 2 479 274 | A1 | 7/2012 | |
| EP | 1 756 136 | B1 | 10/2014 | |
| GB | 2113116 | A | 8/1983 | |
| WO | 96/18731 | A2 | 6/1996 | |
| WO | 02/055737 | A1 | 7/2002 | |
| WO | 02/063963 | A1 | 8/2002 | |
| WO | 03/046146 | A2 | 6/2003 | |
| WO | 2004/104179 | A2 | 12/2004 | |
| WO | 2004/108925 | A1 | 12/2004 | |
| WO | 2005/044982 | A2 | 5/2005 | |
| WO | 2006/073472 | A2 | 7/2006 | |
| WO | 2006/130720 | A2 | 12/2006 | |
| WO | 2006/138553 | A2 | 12/2006 | |
| WO | 2007/140417 | A2 | 12/2007 | |
| WO | 2008/043551 | A1 | 4/2008 | |
| WO | 2009/014415 | A1 | 1/2009 | |
| WO | 2009/025690 | A2 | 2/2009 | |
| WO | 2009/134652 | A1 | 11/2009 | |
| WO | 2009/140313 | A1 | 11/2009 | |
| WO | 2012/135081 | A2 | 10/2012 | |
| WO | 2014/122288 | A1 | 8/2014 | |
| WO | 2015/003060 | A1 | 1/2015 | |
| WO | 2017/041013 | A1 | 3/2017 | |
| WO | WO-2017044827 | A1 * | 3/2017 | C12N 15/1003 |

OTHER PUBLICATIONS

"Thermo Scientific Pierce Cell Lysis Technical Handbook," Version 2, 2009 (54 pages).

Braid et al., "Removal of PCR inhibitors from soil DNA by chemical flocculation," *Journal of Microbiological Methods* 52(3):389-393, 2003 (6 pages).

Chourey et al., "Direct Cellular Lysis/Protein Extraction Protocol for Soil Metaproteomics," *Journal of Proteome Research* 9(12):6615-6622, 2010.

Collins, "Sticky ions in biological systems," *Proc. Natl. Acad. Sci. USA* 92:5553-5557, 1995.

Dijkmans et al., "Rapid method for purification of soil DNA for hybridization and PCR analysis," *Microb Releases* 2:29-34, 1993.

Grasso et al., "Overexpression and Purification of Mammalian Mitochondrial Translational Initiation Factor 2 and Initiation Factor 3," *Methods in Enzymology* 430:59-78, 2007.

Kozlowski, "Proteome-pl: proteome isoelectric point database," *Nucleic Acids Research*: 1-5, 2016.

Likhite et al., "A Unique Method for Isolation and Solubilization of Proteins after Extraction of RNA from Tumor Tissue Using Trizol," *Journal of Biomolecular Techniques* 22(1):37-44, 2011.

Macfarlane et al., "Isolating RNA From Clinical Samples with Catrimox-14 and Lithium Chloride," *Journal of Clinical Laboratory Analysis* 11:132-139, 1997.

Merriam-Webster, "Definition of anti-foaming," retrieved Jul. 4, 2019 from https://www.merriam-webster.com/dictionary/anti-foaming (2 pages).

MO BIO Laboratories, Inc., "AllPrep® Bacterial DNA/RNA/Protein Kit (50)," Catalog No. 47054, 2014 (24 pages).

MO BIO Laboratories, Inc., "NoviPure™ Soil Protein Extraction Kit," Instruction Manual, Catalog No. 30000-20, 2013 (20 pages).

MO BIO Laboratories, Inc., "PowerFecal® DNA Isolation Kit," Instruction Manual, Catalog No. 12830-50, 2013 (16 pages).

MO BIO Laboratories, Inc., "RNA PowerSoil® Total RNA Isolation Kit," Instruction Manual, Catalog No. 12866-25, 2016 (15 pages).

Qiagen, "AllPrep™ DNA/RNA Kits," 2015 (4 pages).

Qiagen, "DNeasy® PowerSoil® Kit Handbook: For the isolation of microbial genomic DNA from all soil types," 2017 (24 pages).

Qiagen, "QIAamp® DNA Stool handbook, For DNA purification from stool samples," Second Edition, Jun. 2012 (44 pages).

Schneegurt et al., "Direct Extraction of DNA from Soils for Studies in Microbial Ecology," *Curr. Issues Mol. Biol.* 5:1-8, 2003.

Shaw et al., "A Simple Procedure for Isolation of DNA, RNA and Protein Fractions from Cultured Animal Cells," *Analytical Biochemistry* 65:125-131, 1975.

Tan et al., "DNA, RNA, and Protein Extraction: The Past and The Present," *Journal of Biomedicine and Biotechnology* 2009(574398):1-10, 2009 (11 pages).

Thatcher, "DNA/RNA Preparation for Molecular Detection," *Clinical Chemistry* 61(1):1-11, 2015.

Triant et al., "Simultaneous Extraction of High-Quality RNA and DNA from Small Tissue Samples," *Journal of Heredity* 100(2):246-250, 2009.

Wikipedia, "Sodium chloride," accessed Sep. 14, 2020 from https://en.wikipedia.org/wiki/Sodium_chloride (9 pages).

Wilkens et al., "Bacteriolysis of *Streptococcus mutans* GS5 by Lysozyme, Proteases, and Sodium Thiocyanate," *Infection and Immunity* 38(3): 1172-1180, 1982.

Willner et al., "Comparison of DNA Extraction Methods for Microbial Community Profiling with an Application to Pediatric Bronchoalveolar Lavage Samples," *PLOS One* 7(4):e34605, 2012 (12 pages).

Yeates et al., "Methods for microbial DNA extraction from soil for PCR amplification," *Biological Procedures Online* 1(1):40-47, 1998.

Zahuczky et al., "Cloning of the bovine leukemia virus proteinase in *Escherichia coli* and comparison of its specificity to that of human T-cell leukemia virus proteinase," *Biochimica et Biophysica Acta* 1478:1-8, 2000.

Sadilek, "Dissertation Thesis," Masaryk University, Faculty of Science, Research Centre for Toxic Compounds in the Environment, Brno, Czech Republic, 178 pages (2017).

Soberón-Chávez, "Biosurfactants, from Genes to Applications," Microbiology Monographs 20, 186 pages (2011).

* cited by examiner

DNA

RNA

DNA

| Sample | [ng/uL] | 260/280 | 260/230 | 340 raw |
|---|---|---|---|---|
| 1 | 13.8 | 1.74 | 0.44 | 0.566 |
| 2 | 15.8 | 1.66 | 0.49 | 0.101 |
| 3 | 15.8 | 1.91 | 0.35 | 0.157 |
| 4 | 15.5 | 1.93 | 0.32 | 0.106 |
| 5 | Out Of Range | 1.87 | 0.73 | 0.073 |
| 6 | Out Of Range | 1.9 | 1.08 | 0.078 |
| 7 | Out Of Range | 1.89 | 1.61 | 0.066 |

RNA

| Sample | [ng/uL] | | | |
|---|---|---|---|---|
| 1 | 34 | 1.7 | 0.91 | 0.532 |
| 2 | 37.3 | 1.71 | 0.79 | 0.561 |
| 3 | 36.4 | 1.71 | 0.9 | 0.534 |
| 4 | 36.8 | 1.75 | 0.93 | 0.584 |
| 5 | 64.6 | 1.95 | 1.36 | 0.41 |
| 6 | 56.7 | 1.93 | 0.89 | 0.462 |
| 7 | 54.7 | 1.91 | 1.17 | 0.505 |

NUCLEIC ACID ISOLATION AND INHIBITOR REMOVAL FROM COMPLEX SAMPLES

BACKGROUND

Technical Field

The present disclosure relates to sample lysis as well as nucleic acid isolation and inhibitor removal from a sample, including a complex sample such as a soil or stool sample.

Description of the Related Art

Isolating nucleic acids with high yields and purity is critical in molecular biology and related fields, including disease diagnosis, forensics, food science, and environmental sciences. The existing technologies suffer from low yields and/or low purity when isolating nucleic acids in certain types of samples, such as environmental samples, like soil samples, and stool samples. The presence of contaminating substances and inhibitors interfere with downstream analysis of the isolated nucleic acids. In particular as the above mentioned sample materials contain huge amounts of in some case quite diverse interfering components and are very complex, a lot of interactions may occur when isolating and purifying biomolecules therefrom. The drawbacks of the existing technologies are partially due to the lack of effective methods for lysing such complex samples. Moreover, the removal of inhibiting components is quite challenging, in particular if several different biomolecules are intended to be isolated and or purified from the same sample.

SUMMARY

The present disclosure provides methods, compositions and kits for isolating nucleic acids while depleting contaminating molecules from a sample. In addition, it provides methods, compositions and kits for preparing a lysate from a sample.

In one aspect, the present disclosure provides a method for isolating nucleic acids from a sample, comprising:

(a) contacting a sample, a lysate of the sample, or a supernatant of the lysate, or a portion of the sample, the lysate or the supernatant with one or more first agents selected from ammonium acetate, ammonium sulfate, potassium acetate, sodium acetate, sodium chloride, cesium acetate, and combinations thereof, and one or more second agents selected from aluminum chloride, erbium (III) acetate, erbium (III) chloride, holmium chloride, hafnium (IV) chloride, zirconium (IV) chloride, and combinations thereof to obtain a mixture, (b) separating the mixture of step (a) into a solid phase and a liquid phase, wherein the one or more second agents are primarily in the solid phase, and (c) isolating nucleic acids from the liquid phase of step (b).

In another aspect, the present application provides a composition for isolating nucleic acids from a sample, comprising, consisting essentially of, or consisting of (i) one or more first agents selected from ammonium acetate, ammonium sulfate, potassium acetate, sodium acetate, sodium chloride, cesium acetate, and combinations thereof, (ii) one or more second agents selected from aluminum chloride, erbium (III) acetate, erbium (III) chloride, holmium chloride, hafnium (IV) chloride, zirconium (IV) chloride, and combinations thereof, and (iii) optionally water.

In another aspect, the present disclosure provides a kit for isolating nucleic acids from a sample, comprising:

(a) the composition provided herein,

OR (b) (i) one or more first agents selected from ammonium acetate, ammonium sulfate, potassium acetate, sodium acetate, sodium chloride, cesium acetate and combinations thereof, and (ii) one or more second agents selected from aluminum chloride, erbium (III) acetate, erbium (III) chloride, holmium chloride, hafnium (IV) chloride, zirconium (IV) chloride, and combinations thereof.

In another aspect, the present disclosure provides a method for preparing a lysate from a sample, comprising:

(a) contacting a sample with a lytic reagent comprising one or more phosphates and a chaotropic agent selected from sodium thiocyanate, sodium carbonate, potassium thiocyanate, ammonium thiocyanate, lithium thiocyanate, lithium perchlorate, guanidine sulfate, and combinations thereof to generate a lysate.

In another aspect, the present disclosure provides a lytic reagent comprising:

(a) a chaotropic agent selected from sodium thiocyanate, sodium carbonate, ammonium thiocyanate, potassium thiocyanate, lithium thiocyanate, lithium perchlorate, guanidine sulfate, and combinations thereof, and (b) one or more phosphates.

In another aspect, the present disclosure provides a kit for preparing a lysate from a sample, comprising:

(i) (a) the lytic reagent provided herein,

OR (b) (1) a chaotropic agent selected from sodium thiocyanate, sodium carbonate, ammonium thiocyanate, potassium thiocyanate, lithium thiocyanate, lithium perchlorate, guanidine sulfate, and combinations thereof, and (2) one or more phosphates.

DETAILED DESCRIPTION

Figure 1:
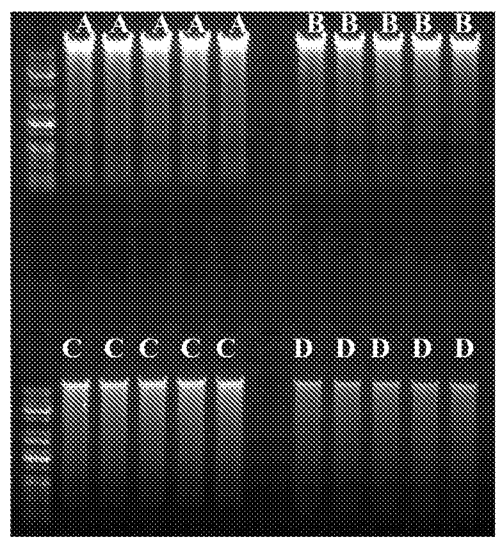
FIG. 1 shows gel electrophoresis of DNA isolated according to Example 1.

The present disclosure provides methods, compositions and kits for effectively lyzing samples to solubilize DNA and RNA from samples, especially from complex samples such as environmental like soil samples and stool samples. The methods provided herein use a lytic reagent that comprises one or more phosphates and one or more relatively mild chaotropic agents to effectively solubilize nucleic acids without significantly degrading such nucleic acids during sample lysis.

In addition, the present disclosure also provides methods, compositions and kits for effectively removing contaminating substances (e.g., inhibitors) from nucleic acids isolated from samples, especially from complex samples such as environmental samples like soil samples and stool samples. The methods provided herein use novel combinations of protein-precipitating agents and tri- or tetra-valent salts in precipitating proteins and contaminating substances and removing them from nucleic acid preparations.

Furthermore, the sample lysis and inhibitor removal methods disclosed herein may be combined with each other to increase nucleic acid yields and purity without sacrificing integrity of isolated nucleic acids.

The methods allow significantly less sample input quantity, for example, from 2 grams to 250 mg, without sacrificing the amount of RNA/gram soil. The methods may use solid support in a spin column format during nucleic acid isolation, which enables automation and facilitates scale-up and high throughput.

In the following description, any ranges provided herein include all the values in the ranges.

It should also be noted that the term "or" is generally employed in its sense including "and/or" (i.e., to mean either one, both, or any combination thereof of the alternatives) unless the content dictates otherwise.

Also, as used in this specification and the appended claims, the singular forms "a," "an," and "the" include plural referents unless the content dictates otherwise.

The terms "include," "have," "comprise" and their variants are used synonymously and to be construed as non-limiting.

The term "a combination thereof" as used herein refers to one of the all possible combinations of the listed items preceding the term. For example, "A, B, C, or a combination thereof" is intended to refer to any one of: A, B, C, AB, AC, BC, or ABC. Similarly, the term "combinations thereof" as used herein refers to all possible combinations of the listed items preceding the term. For instance, "A, B, C, and combinations thereof" is intended to refer to all of: A, B, C, AB, AC, BC, and ABC.

I. Sample Lysis

In one aspect, the present disclosure provides a method for preparing a lysate from a sample that comprises: contacting a sample with a lytic reagent comprising one or more phosphates and one or more relatively mild chaotropic agents. The resulting lysate may be used for isolating or detecting biomolecules of interest (e.g., nucleic acids, proteins).

A. Samples

The sample may be any samples that contain biomolecules of interest, including biological samples, environmental samples and food samples, especially those containing inhibitors that, if present in the preparation of isolated nucleic acids, interfere with downstream analysis of isolated nucleic acids.

The term "biological sample" as used herein refers to a sample obtained from or produced by a biological subject, including but are not limited to, organs, tissues, cells, body fluid (e.g., blood, blood plasma, serum, cerebrospinal fluid, or urine), swab samples, stool samples, and plant samples (e.g., seeds, leaves, roots, stems, flowers, cells or tissues from plant tissue culture). A biological sample may be of prokaryotic origin or eukaryotic origin. In some embodiments, the biological sample is mammalian, especially human.

The method provided herein is especially useful in isolating biomolecules from stool samples. Analysis of biomolecules (e.g., nucleic acids) from stool samples allows detection of bacterial and viral infectious agents, monitoring of changes resulting from diet, use of probiotics and antibiotics, and detection of tumor-specific changes, which may be used as a parameter in the early diagnosis of tumors of the digestive tract.

The term "environmental sample" as used herein refers to any environmental material (i.e., a material contained in the earth and space) that contains biomolecules of interest. The environmental materials may be materials in soil, water, and air. The biomolecules include those from either live or dead organisms in the environmental materials.

The term "soil" as used herein refers to environmental samples of soil (e.g., potting mixtures, mud), sediment (e.g., marine sediment, lake sediment, river sediment), manure (e.g., poultry, like chicken or turkey, manure, horse manure, cattle manure, goat manure, sheep manure), landfill, compost, and the like.

The term "food sample" as used herein refers to materials, substances or compositions for consumption by animals (e.g., human), including raw food, processed food, meat, fish, poultry, vegetables, eggs, dairy products, bakery products, chocolate, peanut butter, beverages, and the like. A food sample may also include a food enrichment culture produced by contacting a food sample with a culture medium and incubating the mixture under conditions suitable for microorganisms if present in the sample to grow.

Due to its high efficiency of solubilizing biomolecules while minimizing degradation of the biomolecules, the method of the present disclosure allows the use of a less amount of a starting material (e.g., less than 1 gram, less than 0.5 gram, or less than 0.25 gram) than traditionally required (e.g., 2 grams) without sacrificing the obtained amount of nucleic acid/gram sample. For example, the starting material may be in the range of 0.01 gram to 1 gram, 0.01 gram to 0.5 gram, 0.01 gram to 0.25 gram, 0.05 gram to 1 gram, 0.05 gram to 0.5 gram, 0.05 gram to 0.25 gram, 0.1 gram to 1 gram, 0.1 gram to 0.5 gram, or 0.1 gram to 0.25 gram.

B. Lytic Reagents

After a sample is collected, the sample is typically lyzed to release biomolecules for subsequent isolation or detection. Sample lysis according to the method disclosed herein uses a lytic reagent that comprises, consists essentially of, or consists of one or more relatively mild chaotropic agents and one or more phosphates (and optionally water).

A chaotropic agent disrupts the structure of, and denatures macromolecules such as proteins and nucleic acids. Chaotropic solutes increase the entropy of the system by interfering with intramolecular interactions mediated by non-covalent forces such as hydrogen bounds, van der Waals forces, and hydrophobic effects, on which macromolecular structure and function depend. Exemplary chaotropic agents include guanidinium chloride, guanidine thiocyanate, urea, or lithium salts.

A "relatively mild" chaotropic agent refers to a chaotropic agent that denatures proteins less than the stronger chaotropic agent, guanidinium thiocyanate (GuSCN) or guandinium chloride (GuCl), but more than the weaker chaotropic agent, sodium chloride. Thus, such relatively mild chaotropic agents may be used to purify and/or isolate proteins as well. Such relatively mild (also referred to as "less aggressive") chaotropic agents include certain Hofmeister series chaotrope cation/anion combinations wherein a relatively strong anion is combined with a relatively weak cation, or a relatively strong cation is combined with a relatively weak anion.

The Hofmeister series is a classification of ions in order of their ability to salt out or salt in proteins. This series of salts have consistent effects on the solubility of proteins and on the stability of secondary and tertiary structure. Anions appear to have a larger effect than cations, and exemplary anions are usually ordered as follows:

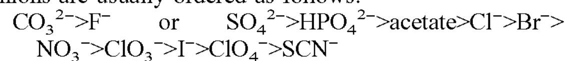

$CO_3^{2-}>F^-$ or $SO_4^{2-}>HPO_4^{2-}>$acetate$>Cl^->Br^->NO_3^->ClO_3^->I^->ClO_4^->SCN^-$ The order of exemplary cations is usually given as follows:

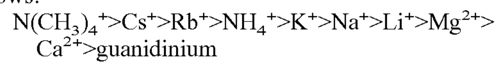

$N(CH_3)_4^+>Cs^+>Rb^+>NH_4^+>K^+>Na^+>Li^+>Mg^{2+}>Ca^{2+}>$guanidinium

Exemplary relatively mild chaotropic agents include NaSCN, $NaCO_3$, KSCN, $NH_4SCN$, LiSCN, $LiClO_4$, guanidine sulfate, and combinations thereof. Preferably, the relatively mild chaotropic agent is NaSCN or $NaCO_3$.

The relatively mild chaotropic agents may include salts having the strong anion, $SCN^-$, paired with a cation weaker than $Mg^{2+}$ in solubilizing proteins; salts having the strong anion, $ClO_4^-$, paired with a cation weaker than $Mg^{2+}$ in solubilizing proteins; and salts having the weak anion, $CO_3^{2-}$, paired with a cation stronger than $NH_4^+$ in solubilizing proteins.

The relatively mild chaotropic agents (e.g., NaSCN) strike a desirable balance between a stronger chaotropic agent such as GuSCN or GuCl and a weaker chaotropic agent such as RbSCN. Such a less aggressive chaotropic agent typically requires an additional mechanism, such as mechanical disruption to lyze a sample, especially a complex sample (e.g., a stool sample). However, the less aggressive chaotropic agent can effectively solubilize biomolecules during homogenization to make them available for downstream isolation or detection steps. Strong chaotropic agents and detergents (e.g., SDS), on the other hand, can achieve complete cell lysis but at the expense of degraded biomolecules (e.g., degraded nucleic acids). The less aggressive chaotropic agents are unique in their capacity to solubilize biomolecules (e.g., nucleic acids) while minimizing degradation of such biomolecules.

The concentration of a relatively mild chaotropic agent in a lytic reagent may be in the range of 0.05 to 5M, such as 0.05 to 0.1M, 0.1 to 0.5M, 0.5 to 1M, 1 to 1.5M, 1.5 to 2M, 2 to 5M, 0.1 to 1M, 0.1 to 1.5M, 0.1 to 2M, 0.1 to 5M, 0.5 to 1.5M, 0.5 to 2M, 0.5 to 5M, 1 to 2M, or 1 to 5M, preferably 0.05 to 0.5M or 0.5 to 2M. The final concentration of a relatively mild chaotropic agent in a lysate (i.e., the mixture of a sample and the lytic reagent) may be 0.01 to 4M, such as 0.01 to 0.05M, 0.05 to 0.1M, 0.1 to 0.5M, 0.5 to 1M, 1 to 1.5M, 1.5 to 2M, 2 to 4M, 0.01 to 0.1M, 0.01 to 0.5M, 0.01 to 1M, 0.01 to 1.5M, 0.01 to 2M, 0.01 to 4M, 0.05 to 0.5M, 0.05 to 1M, 0.05 to 1.5M, 0.05 to 2M, 0.05 to 2M, 0.05 to 4M, 0.1 to 1M, 0.1 to 1.5M, 0.1 to 2M, 0.1 to 4M, 0.5 to 1.5M, 0.5 to 2M, 0.5 to 4M, 1 to 2M, or 1 to 4M, preferably 0.05 to 0.5M or 0.5 to 2M.

For example, the concentration of NaSCN in a lytic reagent may be 0.5 to 2M, preferably 0.8 to 1.2M. The final concentration of NaSCN in a lysate (i.e., the mixture of a sample and the lytic reagent) may be 0.1 to 1.8M, preferably 0.5 to 1.1M.

The concentration of $Na_2CO_3$ in a lytic reagent may be 0.05 to 0.2M, preferably 0.08 to 0.12M. The final concentration of $Na_2CO_3$ in a lysate (i.e., the mixture of a sample and the lytic reagent) may be 0.01 to 0.4M, preferably 0.04 to 0.15 M.

If multiple relatively mild chaotropic agents are present in a lytic reagent, the total concentration of chaotropic agents in combination in the lytic reagent may be in the range of 0.05 to 5M, such as 0.05 to 0.1M, 0.1 to 0.5M, 0.5 to 1M, 1 to 1.5M, 1.5 to 2M, 2 to 5 M, 0.1 to 1M, 0.1 to 1.5M, 0.1 to 2M, 0.1 to 5M, 0.5 to 1.5M, 0.5 to 2M, 0.5 to 5M, 1 to 2M, or 1 to 5M, preferably 0.05 to 0.5M or 0.5 to 2M. The concentration of an individual chaotropic agent in the lytic reagent may be in the range of 0.01 to 4.5M, such as 0.01 to 0.05M, 0.05 to 0.1M, 0.1 to 0.5M, 0.5 to 1M, 1 to 1.5M, 1.5 to 2M, 2 to 4.5 M, 0.01 to 0.1M, 0.01 to 0.5M, 0.01 to 1M, 0.01 to 1.5M, 0.01 to 2M, 0.1 to 1M, 0.1 to 1.5M, 0.1 to 2M, 0.1 to 4.5M, 0.5 to 1.5M, 0.5 to 2M, 0.5 to 4.5M, 1 to 2M, or 1 to 4.5M, preferably 0.01 to 0.5M or 0.1 to 2M. The total final concentration of chaotropic agents in combination in a lysate (i.e., the mixture of a sample and the lytic reagent) may be 0.01 to 4M, such as 0.01 to 0.05M, 0.05 to 0.1M, 0.1 to 0.5M, 0.5 to 1M, 1 to 1.5M, 1.5 to 2M, 2 to 4M, 0.01 to 0.1M, 0.01 to 0.5M, 0.01 to 1M, 0.01 to 0.5M, 0.01 to 2M, 0.01 to 4M, 0.05 to 0.5M, 0.05 to 1M, 0.05 to 1.5M, 0.05 to 2M, 0.05 to 2M, 0.05 to 4M, 0.1 to 1M, 0.1 to 1.5M, 0.1 to 2M, 0.1 to 4M, 0.5 to 1.5M, 0.5 to 2M, 0.5 to 4M, 1 to 2M, or 1 to 4M, preferably 0.05 to 0.5M or 0.5 to 2M. The final concentration of an individual chaotropic agent in the lysate may be 0.001 to 3.5M, such as 0.001 to 0.01M, 0.01 to 0.05M, 0.05 to 0.1M, 0.1 to 0.5M, 0.5 to 1M, 1 to 1.5M, 1.5 to 2M, 2 to 3.5M, 0.001 to 0.1M, 0.001 to 0.5M, 0.001 to 1M, 0.001 to 1.5M, 0.001 to 2M, 0.001 to 3.5M, 0.01 to 0.1M, 0.01 to 0.5M, 0.01 to 1M, 0.01 to 1.5M, 0.01 to 2M, 0.01 to 3.5M, 0.05 to 0.5M, 0.05 to 1M, 0.05 to 1.5M, 0.05 to 2M, 0.05 to 2M, 0.05 to 3.5M, 0.1 to 1M, 0.1 to 1.5M, 0.1 to 2M, 0.1 to 3.5M, 0.5 to 1.5M, 0.5 to 2M, 0.5 to 3.5M, 1 to 2M, or 1 to 3.5M, preferably 0.01 to 0.5M or 0.1 to 2M.

In addition to one or more relatively mild chaotropic agents, a lytic reagent may further comprise one or more phosphates. Phosphate is especially useful in achieving uniform disruption of soil particles, solubilizing soil organic matter, and extracting humic substances from soil. In addition, without wishing to be bound by theory, it is believed that the free phosphate group ($PO_4^{3-}$) also prevents or reduces complex formation between an inhibitor removing agent (e.g., $AlCl_3$) and the phosphodiester groups of nucleic acids by competitively interacting with the inhibitor removing agent. Exemplary phosphates include phosphate monobasics, phosphate dibasics, and phosphate tribasics, and other compounds that contain one or more free phosphate groups, such as sodium phosphate monobasic, sodium phosphate dibasic, sodium phosphate, potassium phosphate monobasic, potassium phosphate dibasic, potassium phosphate, ammonium phosphate monobasic, ammonium phosphate dibasic, ammonium phosphate, lithium phosphate monobasic, lithium phosphate dibasic, lithium phosphate, trisodium phosphate, sodium poly(vinylphosphonate), sodium hexametaphosphate, pyrophosphate, sodium triphosphate, sodium polyphosphate, other phosphorus-containing oxyanions, and combinations thereof. The cationic moieties in the phosphates include but are not limited to ammonium, sodium, potassium, and lithium.

The concentration of a phosphate in a lytic reagent may be 0.05 to 0.5M, preferably 0.1 to 0.2M. The final concentration of phosphate in a lysate (i.e., the mixture of a sample and the lytic reagent) may be 0.01 to 0.4M, preferably 0.1 to 0.2M. If multiple phosphates are present in a lytic reagent, the total concentration of phosphates in combination in the lytic reagent may be in the range of may be 0.05 to 0.5M, preferably 0.1 to 0.2M. The concentration of an individual phosphate in the lytic reagent may be in the range of 0.01 to 0.45M, such as 0.01 to 0.1M, 0.1 to 0.2M, 0.2 to 0.3M, 0.3 to 0.45M, preferably 0.01 to 0.2M. The total final concentration of phosphates in combination in a lysate (i.e., the mixture of a sample and the lytic reagent) may be 0.01 to 0.4M, 0.01 to 0.05M, 0.05 to 0.1M, 0.1 to 0.4M, preferably 0.1 to 0.2M. The final concentration of an individual phosphate in the lysate may be in the range of 0.001 to 0.35M, such as 0.001 to 0.01M, 0.01 to 0.05M, 0.05 to 0.1M, 0.1 to 0.35M, 0.1 to 0.2M, 0.2 to 0.35M, preferably 0.01 to 0.2M.

A lytic reagent may also include one or more detergents, including nonionic, cationic, anionic (sodium dodecyl sulfate) or zwitterionic detergents. Exemplary detergents include sodium dodecyl sulfate (SDS), sarkosyl, sodium lauryl sarcosinate, cetyltrimethyl ammonium bromide (CTAB), cholic acid, deoxycholic acid, benzamidotaurocholate (BATC), octyl phenol polyethoxylate, polyoxyethylene sorbitan monolaurate, tert-octylphenoxy poly(oxyethylene) ethanol, 1,4-piperazinebis-(ethanesulfonic acid), N-(2-acetamido)-2-aminoethanesulfonic acid, polyethylene glycol-tert-octylphenyl ether (TRITON® X-100), (1,1,3,3-tetramethylbutyl)phenyl-polyethylene glycol (TRITON® X-114), and combinations thereof.

The total concentration of detergents in combination in a lytic reagent may be in the range of 0.01% to 15% (v/v) if the detergent(s) is liquid or 0.01% to 15% (w/v) if the detergent(s) is solid. The concentration of an individual detergent in the lytic reagent may be in the range of 0.001 to 15%, such as 0.005 to 12%, 0.01 to 10%, 0.1 to 8%, 0.05 to 6%, 0.1 to 4%, 0.5 to 2%, 0.8 to 1%, preferably 0.01 to 15%. The total final concentration of the detergents in combination in a lysate (i.e., the mixture of a sample and the lytic reagent) may be 0.005% to 12%, such as 0.005% to 0.05%, 0.05% to 0.5%, 0.5% to 5%, 5% to 12%, 0.05% to 10%, 0.1% to 10%, or 0.5% to 5%. The total final concentration of an individual detergent in the lytic reagent may be in the range of 0.001 to 12%, such as 0.005 to 10%, 0.01 to 8%, 0.05 to 6%, 0.05 to 6%, 0.1 to 4%, 0.2 to 2%, 0.5 to 1%, preferably 0.001 to 12%.

In certain other embodiments, a lytic reagent does not include any detergent, such as SDS.

A lytic reagent may additionally contain one or more blocking agents that block or reduce the interaction between contaminants in a sample and nucleic acids liberated during lysis and solubilization. Exemplary blocking agents include casein, polyacrylic acid and polystyrene sulfonate. Such blocking agents are useful in blocking electrostatic interactions between particles in a sample (e.g., soil particles) having positively charged groups (e.g., metal ions) and nucleic acids released from the sample. Such interactions, if not disrupted, can lead to significant decreases in nucleic acid yields from the sample.

The total concentration of the blocking agents in combination in a lytic reagent may be in the range of 0.01 to 0.5 M of relevant functional group (e.g., carboxylates, in the case of polyacrylic acid; sulfonates, phosphates). The concentration of an individual blocking agent in the lytic reagent may be in the range of 0.001 to 0.5M. The total final concentration of the blocking agents in combination in a lysate (i.e., the mixture of a sample and the lytic reagent) may be in the range of 2 to 400 mM. The final concentration of an individual blocking agent in the lytic reagent may be in the range of 0.2 to 400 mM. In certain other embodiments, a lytic reagent does not include any blocking agent.

A lytic reagent may further contain one or more salts other than the chaotropic agents or phosphates described above. Exemplary salts include NaCl, NaF, LiCl, NaBr, NaI, RbCl, CsCl, RbBr, CsBr, RbI, CsI, and combinations thereof. The total concentration of the salts in combination in the lytic reagent may be in the range of 10 to 500 mM, such as 30 to 300 mM or 50 to 200 mM. The concentration of an individual salt in the lytic reagent may be in the range of 1 to 500 mM, such as 10 to 200 mM or 25 to 100 mM. In certain other embodiments, a lytic reagent does not include any additional salts (e.g., NaCl).

A lytic reagent may further contain one or more buffer substances so that lysis occurs at a stable pH. The pH of the lytic reagent may be in the range of pH 6 to pH 12, such as pH 6 to pH 8, pH 7 to pH 9, pH 8 to pH 10, and pH 8 to pH 11, and pH 7 to pH10.

The lytic reagent that comprises, consists essentially of, or consists of one or more relatively mild chaotropic agents and one or more phosphates, both as described above may be in its solid state. Preferably, the lytic reagent is a solution that comprises, consists essentially of, or consists of one or more above-described relatively mild chaotropic agents, one or more above-described phosphates, and water. Preferably, the one or more relatively mild chaotropic agents comprise or are NaSCN or $NaCO_3$, especially NaSCN. The one or more phosphates preferably comprise or are sodium phosphate dibasic. An exemplary preferred lytic reagent comprises, consists essentially of, or consists of 0.5 to 2M NaSCN and 0.1 to 0.2M $Na_2HPO_4$. Another exemplary preferred lytic reagent comprises, consists essentially of, or consists of 0.05 to 0.5M $Na_2CO_3$ and 0.1 to 0.2M $Na_2HPO_4$.

C. Lysis Process

The method for preparing a lysate from a sample provided herein comprises contacting a sample with one or more lytic reagents described above under conditions appropriate for biomolecules of interest for a sufficient time to solubilize the biomolecules without significant degradation of such molecules. Although certain aspects of this disclosure described below focus on nucleic acid isolation, the lytic reagents described above are not only useful for lysing samples for nucleic acid isolation, but also useful for lysing samples for other purposes, such as isolating, purifying and/or detecting proteins.

The lytic reagents that comprise, consist essentially of, or consist of one or more relatively mild chaotropic agent and one or more phosphates may be used in combination with one or more other sample lysis methods, such as physical disruption and enzymatic lysis.

Physical disruption of sample includes sonication, temperature change, mechanical disruption using a mechanical force, shear force, mechanical vibration, or a vortexer, or a combination of such methods.

Mechanical disruption may include the use of bead beating and/or homogenizing methods. The beads useful for mechanical disruptions may be made of or comprise glass, ceramic, metal, mineral, or a combination of two or more of such materials. The size of the beads may range from 0.05 mm to 3 mm. Exemplary beads include 0.7 mm garnet beads, 0.15 mm garnet beads, 0.1 mm glass beads, 0.5 mm glass beads, 0.1 mm ceramic beads, 0.5 mm ceramic beads, 1.4 mm ceramic beads, 0.1 mm yttrium-stabilized zirconium beads, 0.5 mm yttrium-stabilized zirconium beads, or a combination of such beads (e.g., 0.1 mm glass beads and 0.5 mm glass beads in the same amount). In certain preferred embodiments, the beads are high density beads with density (g/cc) at least 6.0, such as yttrium-stabilized zirconium beads, cerium stabilized beads, and stainless steel beads. Bead beating may be performed using a vortex mixer with bead tube adapter or bead beater, such as TissueLyzer II (QIAGEN), AMBION™ Vortex Adapter (Thermo Fisher Scientific, Waltham, MA) and the Omini Bead Rupter Homogenizer, OMNI Int'l, Kennesaw, GA), and various homogenizers by OPS Diagnostics. The speed and duration of bead beating may vary depending on the type and size of the sample (see e.g., Gibbons et al., Bead Beating: A Primer, OPS Diagnostics, LLC). For example, bead beating may be performed at the maximum speed of a bead beater for 1 to 20 minutes, such as 5 to 10 minutes, 10 to 20 minutes, or 5 to 15 minutes.

The lytic reagents disclosed herein are preferably used in combination with mechanical disruption (e.g., bead beating) in isolating biomolecules (e.g., DNA, RNA, and/or proteins) from a complex sample, such as a stool sample. The biomolecules may be of a microbial origin.

The lytic reagents may also be used in combination with enzymatic lysis, which includes the use of an amylase, cellulase, lipase, proteases or the like.

If the lytic reagents are used to generate a lysate for isolating proteins, the lysis may be performed at a low temperature (e.g., 4° C.) to avoid or reduce protein denaturation. In some other embodiments where downstream analysis (e.g., mass spectrometry analysis) of isolated proteins does not require non-denatured proteins, the lysis may be performed at a higher temperature (e.g., 20 to 25° C.). In addition, proteases are generally not included in the lytic reagent. Instead, preferably, proteinase inhibitors (e.g., Halt protease inhibitors from Thermo Fisher) are added to the sample material, the lytic reagent, or a mixture of the sample material and the lytic reagent shortly prior to sample lysis to prevent or reduce protein degradation during sample lysis and subsequent protein isolation. Similarly, a reducing agent (e.g., beta-mercaptoethanol) may be added to the sample material, the lytic reagent, or a mixture of the sample material and the lytic reagent shortly prior to sample lysis to avoid the loss of activity of proteins or enzymes caused by oxidization.

The resulting lysate may be directly used in a subsequent step (e.g., inhibitor removal) in a method of isolating biomolecules from a sample. Preferably, the lysate is separated into a liquid phase that comprises biomolecules released from the sample and a solid phase that contains solid particles or residues from the sample by filtration, sedimentation or preferably centrifugation. The resulting liquid phase (i.e., supernatant) or a portion thereof may be used to isolate biomolecules and/or remove inhibitors.

D. Kits

In a related aspect, the present disclosure provides a kit for preparing a lysate from a sample that comprises (a) the lytic reagent described above, or (b) the one or more phosphates and the one or more relatively mild chaotropic agents of the lytic reagent provided separately.

The kit may additionally comprise a homogenizing material (i.e., a substance useful in homogenizing a sample such as beads, preferably high density beads) for mechanically disrupting a sample (e.g., a stool sample).

The kit may further comprise one or more first agents functioning as one or more protein precipitating agents. Exemplary protein precipitating agents include ammonium acetate, ammonium sulfate, potassium acetate, sodium acetate, and sodium chloride, preferably sodium acetate and cesium acetate, as described below.

Alternatively, the kit may further comprise one or more first agents functioning as one or more molecular screens that competitively bind functional groups of proteins in a sample and thus prevent such groups from interacting with the multivalent cation of a multivalent salt useful in depleting contaminants from the sample. Such agents are useful in generating lysates for isolating proteins and optionally other biomolecules (e.g., nucleic acids). Molecular screens may be selected from low molecular weight carboxylates, low molecular weight sulfates, carboxylate polymers, sulfonated polymers, and mixtures thereof. Exemplary molecular screens include amino acids; salts of short chain fatty acids, such as sodium butyrate; sodium polystyrene sulfonate; sodium polyacrylic acid; preferably ammonium sulfate, ammonium glycolate, sulfoacetic acid, ammonium formate, sodium acetate, cesium acetate, ammonium acetate, beta-alanine, guanidine sulfate, histidine, glycine, and combinations thereof.

Some of the first agents (e.g., ammonium acetate) may function as a protein precipitating agent at a relatively high concentration (e.g., at 1 to 2 M in a mixture comprising a lysate, the first agent, and one or more second agents as described below) but as a molecular screen at a relatively low concentration (e.g., at a concentration 5 to 15 times less than the concentration when functioning as a protein precipitation agent).

The kit may further comprise one or more second agents functioning as one or more inhibitor removing agents. Exemplary inhibitor removing agents include aluminum ammonium sulfate, aluminum ammonium sulfate dodecahydrate, ammonium sulfate, aluminum potassium sulfate, aluminum chlorohydrate, calcium oxide, iron (III) chloride, iron (II) sulfate, sodium aluminate, sodium silicate, magnesium chloride, aluminum chloride, aluminum sulfate, erbium (III) acetate, erbium (III) chloride, holmium chloride, zirconium (IV) chloride, hafnium (IV) chloride, and combinations thereof. Preferably, the inhibitor removing agents include aluminum chloride, aluminum sulfate, erbium (III) acetate, erbium (III) chloride, holmium chloride, zirconium (IV) chloride, hafnium (IV) chloride, and combinations thereof.

The one or more first agents and the one or more second agents may form a composition either in solid form or as a solution.

In the embodiments where the composition is a solution and the one or more first agents function as a protein precipitating agent, the total concentration of the one or more first agents in the solution is in the range of 0.5 M to 10M, 1 to 8M, or 1.5 to 7.5M, preferably 0.5 to 5M, 0.5 to 7.5M, 2.5 to 5M, 2.5 to 7.5M, 1 to 8M or 1.5 to 7.5M; and/or the total concentration of the one or more second agents in the solution is in the range of 10 to 500 mM, such as 10 to 100 mM, 100 to 200 mM, 200 to 300 mM, 300 to 400 mM, 400 to 500 mM, 10 to 200 mM, 10 to 300 mM, 10 to 400 mM, 100 to 300 mM, 100 to 400 mM, 100 to 500 mM, 200 to 400 mM, 200 to 500 mM, and 300 to 500 mM, preferably 10 to 200 mM, 10 to 500 mM, 50 to 200 mM, 50 to 500 mM or 75 to 150 mM. If the composition comprises multiple first agents, the concentration of an individual first agent may be in the range of 0.1 to 9.5M, such as 0.1 to 0.5M, 0.5 to 2.5M, 2.5 to 5M, 5 to 7.5M, 7.5 to 9.5M, 0.1 to 2.5M, 0.1 to 5M, 0.1 to 7.5M, 0.5 to 5M, 0.5 to 7.5M, 0.5 to 9.5M, 2.5 to 7.5M, 2.5 to 9.5M, 5 to 9.5M, preferably 0.1 to 5M, 0.5 to 7.5M, 2.5 to 5M, 2.5 to 7.5M, 1 to 8M or 1.5 to 7.5M. If the composition comprises multiple second agents, the concentration of an individual second agent may be in the range of 1 to 450 mM, such as 1 to 10 mM, 10 to 100 mM, 100 to 200 mM, 200 to 300 mM, 300 to 400 mM, 400 to 450 mM, 1 to 200 mM, 1 to 300 mM, 1 to 400 mM, 1 to 450 mM, 100 to 300 mM, 100 to 400 mM, 100 to 450 mM, 200 to 400 mM, 200 to 450 mM, 300 to 450 mM, preferably 1 to 200 mM, 10 to 450 mM, 50 to 200 mM, 50 to 450 mM or 75 to 150 mM.

In the embodiments where the composition is a solution and the one or more first agents function as molecular screen(s), the total concentration of the one or more first agents in the solution is in the range of 0.1 to 1M, such as 0.1 to 0.25M, 0.25 to 0.5M, 0.5 to 0.75M, 0.75 to 1M, 0.1 to 0.5M, 0.1 to 0.75M, 0.25 to 0.75M, 0.1 to 0.95M, 0.25 to 1M, or 0.5 to 1M, preferably 0.1 to 0.75M; and/or the total concentration of the one or more second agents in the solution is in the range of 10 to 500 mM, such as 10 to 100 mM, 100 to 200 mM, 200 to 300 mM, 300 to 400 mM, 400 to 500 mM, 100 to 300 mM, 100 to 400 mM, 100 to 500 mM, 200 to 400 mM, 200 to 500 mM, 300 to 500 mM, preferably 10 to 200 mM, 10 to 500 mM, 50 to 200 mM, 50 to 500 mM or 75 to 150 mM. If the composition comprises multiple first agents, the concentration of an individual first agent may be in the range of 0.01 to 0.95M, such as 0.01 to 0.1M, 0.1 to 0.25M, 0.25 to 0.5M, 0.5 to 0.75M, 0.75 to 0.95M, 0.01 to 0.25M, 0.01 to 0.5M, 0.01 to 0.75M, 0.1 to 0.5M, 0.1 to 0.75M, 0.25 to 0.75M, 0.25 to 0.95M, or 0.5 to 0.95M, preferably 0.01 to 0.75M. If the composition comprises multiple second agents, the concentration of an individual second agent may be in the range of 1 to 450 mM, such as 1 to 10 mM, 10 to 100 mM, 100 to 200 mM, 200 to 300 mM, 300 to 400 mM, 400 to 450 mM, 100 to 300 mM, 100 to 400 mM, 100 to 450 mM, 200 to 400 mM, 200 to 450 mM, 300 to 450 mM, preferably 1 to 100 mM, 10 to 200 mM, 10 to 450 mM, 50 to 200 mM, 50 to 450 mM or 75 to 150 mM.

The kit may further comprise one or more of the following components:

a protein binding solution, a protein wash solution, a protein elution solution, a nucleic acid-binding solid support (e.g., DNA-binding solid support, RNA-binding solid support, and solid support capable of binding both DNA and RNA), a DNA binding solution, a DNA wash solution, a DNA elution solution, a RNA binding solution, a RNA wash solution, a RNA elution solution, and one or more vessels or containers (e.g., collection tubes).

A "protein binding solution" refers to a solution that facilitates or strengthens the binding of proteins to a protein-binding solid support. The binding solution may comprise a buffer solution (e.g., citrate buffer) and one or more salts (e.g., NaCl). The final concentration of the salt(s) in the binding mixture may be in the range of 1 to 5M, such as 2 to 3M.

A "protein-binding solid support" refers to a solid support capable of binding proteins, including proteins in general (i.e., total proteins) or specific proteins of interest. Exemplary protein-binding solid supports include silica spin filter membranes, silica spin columns, silica-coated magnetic beads, diatomaceous earth, and finely divided suspensions of silica particles.

A "protein wash solution" refers to a solution useful in removing contaminants from proteins bound to a protein-binding solid support, such as solutions containing ethanol.

A "protein elution solution" refers to a solution useful in eluting proteins bound to a protein-binding solid support. Exemplary protein elution solutions include buffer solutions (e.g., a HEPES (4-(2-hydroxyethyl)-1-piperazineethane-sulfonic acid buffer) that optionally contain a detergent (e.g., SDS).

Solid supports and solutions useful in nucleic acid isolations are as described in the "Nucleic Acid Isolation" section below.

In a related aspect, the present disclosure provides the use of the above-described kit in preparing a lysate and/or isolating biomolecules from a sample.

II. Nucleic Acid Isolation

In another aspect, the present disclosure provides a method for isolating nucleic acids from a sample that comprises:

(a) contacting a sample, a lysate of the sample, or a supernatant of the lysate, or a portion of the sample, the lysate or the supernatant with one or more first agents selected from ammonium acetate, ammonium sulfate, potassium acetate, sodium acetate, sodium chloride, cesium acetate, and combinations thereof, and one or more second agents selected from aluminum chloride, erbium (III) acetate, erbium (III) chloride, holmium chloride, hafnium (IV) chloride, zirconium (IV) chloride, and combinations thereof to obtain a mixture, (b) separating the mixture of step (a) into a solid phase and a liquid phase, wherein the one or more second agents are primarily in the solid phase, and (c) isolating nucleic acids from the liquid phase of step (b).

A. Methods

1. Sample Lysis

Samples for isolating nucleic acids according to the methods provided herein may be any samples that contain nucleic acids, including biological samples, environmental samples and food samples, especially those containing inhibitors that, if present in the preparation of isolated nucleic acids, would interfere with downstream analysis of isolated nucleic acids.

Various types of samples are as described in section "I. Sample Lysis," subsection "A. Samples" above. Preferred samples include soil samples and stool samples.

The amount of a sample needed as a starting material may vary depending on the downstream analysis of nucleic acids isolated from the sample. Due to its high efficiency in isolating nucleic acids while depleting inhibitors, the method of the present disclosure allows the use of a less amount of a starting material (e.g., less than 1 gram, less than 0.5 gram or less than 0.25 gram) than traditionally required (e.g., 2 grams) without sacrificing the obtained amount of nucleic acid/gram sample. For example, the starting material may be in the range of 0.01 gram to 1 gram, 0.01 gram to 0.5 gram, 0.01 gram to 0.25 gram, 0.05 gram to 1 gram, 0.05 gram to 0.5 gram, 0.05 gram to 0.25 gram, 0.1 gram to 1 gram, 0.1 gram to 0.5 gram, or 0.1 gram to 0.25 gram.

After a sample is collected, the sample is typically lyzed to release nucleic acids before such molecules are isolated. Sample lysis may be performed at the same time as inhibitor removal, and preferably prior to inhibitor removal.

Sample lysis may be performed by physical disruption, chemical lysis, enzymatic lysis, or a combination thereof. Depending on a given sample type and organisms present in the sample, different sample disruption methods may be used. For example, although human cells and viral capsids are easily lysed by salts or detergents, bacterial spores or oocysts require more aggressive chemical, enzymatic or physical methods.

Physical disruption and enzymatic lysis are as described in section "I. Sample Lysis," subsection "C. Lysis process" above.

Chemical lysis includes the use of a lytic reagent comprising one or more chaotropic agents. Exemplary chaotropic agents include guanidinium chloride, guanidine thiocyanate, urea, or lithium salts. Preferably, the one or more chaotropic agent(s) are relatively mild chaotropic agent(s) as described in section "I. Sample Lysis," subsection "B. Lysis Reagents" above.

The total concentration of one or more chaotropic agents in a lytic reagent may be in the range of 0.05 to 5M, such as 0.05 to 0.1M, 0.1 to 0.5M, 0.5 to 1M, 1 to 1.5M, 1.5 to 2M, 2 to 5 M, 0.1 to 1M, 0.1 to 1.5M, 0.1 to 2M, 0.1 to 5M, 0.5 to 1.5M, 0.5 to 2M, 0.5 to 5M, 1 to 2M, or 1 to 5M, preferably 0.05 to 0.5M or 0.5 to 2M. If multiple chaotropic agents are present in the lytic reagent, the concentration of an individual chaotropic agent in the lytic reagent may be in the range of 0.01 to 4.5M, such as 0.01 to 0.05M, 0.05 to 0.1M, 0.1 to 0.5M, 0.5 to 1M, 1 to 1.5M, 1.5 to 2M, 2 to 4.5 M, 0.01 to 0.1M, 0.01 to 0.5M, 0.01 to 1M, 0.01 to 1.5M, 0.01 to 2M, 0.1 to 1M, 0.1 to 1.5M, 0.1 to 2M, 0.1 to 4.5M, 0.5 to 1.5M, 0.5 to 2M, 0.5 to 4.5M, 1 to 2M, or 1 to 4.5M, preferably 0.01 to 0.5M or 0.1 to 2M.

The final total concentration of the one or more chaotropic agents in a lysate (i.e., the mixture of a sample and the lytic reagent) may be 0.01 to 4M, such as 0.01 to 0.05M, 0.05 to 0.1M, 0.1 to 0.5M, 0.5 to 1M, 1 to 1.5M, 1.5 to 2M, 2 to 4M, 0.01 to 0.1M, 0.01 to 0.5M, 0.01 to 1M, 0.01 to 1.5M, 0.01 to 2M, 0.01 to 4M, 0.05 to 0.5M, 0.05 to 1M, 0.05 to 1.5M, 0.05 to 2M, 0.05 to 2M, 0.05 to 4M, 0.1 to 1M, 0.1 to 1.5M, 0.1 to 2M, 0.1 to 4M, 0.5 to 1.5M, 0.5 to 2M, 0.5 to 4M, 1 to 2M, or 1 to 4M, preferably 0.05 to 0.5M or 0.5 to 2M. If multiple chaotropic agents are present in the lysate, the concentration of an individual chaotropic agent in the lysate may be in the range of 0.001 to 3.5M, such as 0.001 to 0.01M, 0.01 to 0.05M, 0.05 to 0.1 M, 0.1 to 0.5M, 0.5 to 1M, 1 to 1.5M, 1.5 to 2M, 2 to 3.5M, 0.001 to 0.1M, 0.001 to 0.5M, 0.001 to 1M, 0.001 to 1.5M, 0.001 to 2M, 0.001 to 3.5M, 0.01 to 0.1M, 0.01 to 0.5M, 0.01 to 1M, 0.01 to 1.5M, 0.01 to 2M, 0.01 to 3.5M, 0.05 to 0.5M, 0.05 to 1M, 0.05 to 1.5M, 0.05 to 2M, 0.05 to 2M, 0.05 to 3.5M, 0.1 to 1M, 0.1 to 1.5M, 0.1 to 2M, 0.1 to 3.5M, 0.5 to 1.5M, 0.5 to 2M, 0.5 to 3.5M, 1 to 2M, or 1 to 3.5M, preferably 0.01 to 0.5M or 0.1 to 2M.

The lytic reagent may further comprise one or more phosphates as described in the "Sample Lysis" section above. The total concentration of the one or more phosphates in a lytic reagent may be 0.05 to 0.5M, preferably 0.1 to 0.2M. The concentration of an individual phosphate in the lytic reagent (if multiple phosphates are present in the lytic reagent) may be in the range of 0.01 to 0.45M, such as 0.01 to 0.1M, 0.1 to 0.2M, 0.2 to 0.3M, 0.3 to 0.45M, preferably 0.01 to 0.2M. The final total concentration of the one or more phosphates in a lysate (i.e., the mixture of a sample and the lytic reagent) may be 0.01 to 0.4M, preferably 0.1 to 0.2M. The final concentration of an individual phosphate in the lysate (if multiple phosphates are present in the lysate) may be in the range of 0.001 to 0.35M, such as 0.001 to 0.01M, 0.01 to 0.05M, 0.05 to 0.1M, 0.1 to 0.35M, 0.1 to 0.2M, 0.2 to 0.35M, preferably 0.01 to 0.2M.

A lytic reagent may further comprise one or more of the following components: one or more detergents, one or more blocking agents, one or more salts other than the chaotropic agents or phosphates described above, and one or more buffer substances so that lysis occurs at a stable pH. Such additional components and their concentrations are also as described in section "I. Sample Lysis," subsection "B. Lytic reagents" above.

Preferably, a lytic reagent comprising one or more relatively mild chaotropic agents and one or more phosphates described in section "I. Sample Lysis," subsection "B. Lytic reagents" above is used in the method for isolating nucleic acids from a sample provided herein.

The lysate of a sample may be directly used in step (a) in the method of isolating nucleic acids disclosed herein. Preferably, the lysate is separated into a liquid phase that comprises nucleic acids released from the sample and a solid phase that contains solid particles or residues from the sample by filtration, sedimentation or preferably centrifugation. The resulting liquid phase (i.e., supernatant) or a portion thereof may be used to isolate nucleic acids and remove inhibitors.

2. Inhibitor Removal

The method provided herein isolates nucleic acids from a sample and removes inhibitors from the isolated nucleic acids, allowing effective downstream analysis of isolated nucleic acids. Specifically, step (a) of the method disclosed herein is to contact a sample, a lysate of the sample, a supernatant of the sample, or a portion of the sample, the lysate or the supernatant with one or more first agents selected from ammonium acetate, ammonium sulfate, potassium acetate, sodium acetate, sodium chloride, cesium acetate, and combinations thereof, and one or more second agents selected from aluminum chloride, erbium (III) acetate, erbium (III) chloride, holmium chloride, hafnium (IV) chloride, zirconium (IV) chloride, and combinations thereof to obtain a mixture. Step (b) is to separate the mixture of step (a) into a solid phase and a liquid phase, wherein the one or more inhibitor removing agents are primarily in the solid phase and thus removed from the liquid phase, which is subsequently used in isolating nucleic acids.

The one or more first agents are selected from ammonium acetate, ammonium sulfate, potassium acetate, sodium acetate, sodium chloride, cesium acetate, preferably ammonium acetate, sodium acetate and cesium acetate.

In certain embodiments, the one or more first agents do not include sodium chloride or potassium acetate.

The total concentration of the first agents in combination in the mixture of step (a) may be in the range of 0.1 to 3M, such as 0.1 to 0.25M, 0.1 to 0.5M, 0.1 to 1M, 0.1 to 1.5M, 0.1 to 2M, 0.1 to 2.5M, 0.1 to 3M, 0.25 to 0.5M, 0.5 to 1M, 1 to 1.5M, 1.5 to 2M, 2 to 2.5M, 2.5 to 3M, 0.25 to 1M, 0.25 to 1.5M, 0.25 to 2M, 0.25 to 2.5M, 0.25 to 3M, 0.5 to 1.5M, 0.5 to 2M, 0.5 to 2.5M, 0.5 to 3M, 1 to 2M, 1 to 2.5M, 1 to 3M, 2 to 3M, preferably 0.5 to 2.5M or 1 to 2M. If multiple first agents are present in the mixture of step (a), the concentration of an individual first agent in the mixture of step (a) may be in the range of 0.01 to 2.5M, such as 0.01 to 0.1M, 0.1 to 0.25M, 0.25 to 0.5M, 0.5 to 1M, 1 to 1.5M, 1.5 to 2M, 2 to 2.5M, 0.01 to 0.5M, 0.01 to 1M, 0.01 to 1.5M, 0.01 to 2M, 0.01 to 2.5M, 0.1 to 0.5M, 0.1 to 1M, 0.1 to 1.5M, 0.1 to 2M, 0.1 to 2.5M, 0.25 to 1M, 0.25 to 1.5M, 0.25 to 2M, 0.25 to 2.5M, 0.5 to 1.5M, 0.5 to 2M, 0.5 to 2.5M, 1 to 2M, 1 to 2.5M, preferably 0.1 to 2M or 0.5 to 2M.

The one or more first agents may function in step (a) as protein precipitating agent(s), and be referred to as "protein precipitating agent(s)."

The one or more second agents function as inhibitor removing agent(s), and may be referred to as "inhibitor removing agent(s)." The inhibitor removing agent is a tri- or tetra-valent salt that contains a cation having a valence of three or four. Exemplary inhibitor removing agents include aluminum chloride, erbium (III) acetate, erbium (III) chloride, holmium chloride, zirconium (IV) chloride, hafnium (IV) chloride, and combinations thereof, preferably aluminum chloride, erbium (III) acetate, erbium (III) chloride, holmium chloride, more preferably aluminum chloride.

The total concentration of the one or more second agents in the mixture of step (a) may be in the range of 1 to 150 mM, such as 1 to 5 mM, 5 to 25 mM, 25 to 50 mM, 50 to 75 mM, 75 to 100 mM, 100 to 150 mM, 1 to 25 mM, 1 to 50 mM, 1 to 75 mM, 1 to 100 mM, 1 to 150 mM, 5 to 50 mM, 5 to 75 mM, 5 to 100 mM, 5 to 150 mM, 25 to 75 mM, 25 to 100 mM, 25 to 150 mM, 50 to 100 mM, 50 to 150 mM, 75 to 150 mM, preferably, 5 to 25 mM or 5 to 50 mM. If multiple second agents are present in the mixture of step (a), the concentration of an individual second agent in the mixture of step (a) may be in the range of 0.1 to 145 mM, such as 0.1 to 1 mM, 1 to 5 mM, 5 to 25 mM, 25 to 50 mM, 50 to 75 mM, 75 to 100 mM, 100 to 145 mM, 0.1 to 5 mM, 0.1 to 25 mM, 0.1 to 50 mM, 0.1 to 75 mM, 0.1 to 100 mM, 0.1 to 145 mM, 1 to 25 mM, 1 to 50 mM, 1 to 75 mM, 1 to 100 mM, 1 to 145 mM, 5 to 50 mM, 5 to 75 mM, 5 to 100 mM, 5 to 145 mM, 25 to 75 mM, 25 to 100 mM, 25 to 145 mM, 50 to 100 mM, 50 to 145 mM, 75 to 145 mM, preferably, 1 to 25 mM or 5 to 50 mM.

Any of the first agents, including when functioning as precipitating agents, described above may be used in combination with any of the second agents, including when functioning as inhibitor removing agents, described above in the inhibitor removal process of the method provided herein. For example, ammonium acetate may be combined with the following inhibitor removing agent: aluminum chloride, erbium (III) acetate, erbium (III) chloride, holmium chloride, zirconium (IV) chloride, hafnium (IV) chloride, or a combination thereof. Similarly, sodium acetate may be combined with the following inhibitor removing agent: aluminum chloride, erbium (III) acetate, erbium (III) chloride, holmium chloride, zirconium (IV) chloride, hafnium (IV) chloride, or a combination thereof; and cesium acetate may be combined with the following inhibitor removing agent: aluminum chloride, erbium (III) acetate, erbium (III) chloride, holmium chloride, zirconium (IV) chloride, hafnium (IV) chloride, or a combination thereof. Another alternative is to combine aluminum chloride with the following protein precipitating agent: ammonium acetate, ammonium sulfate, potassium acetate, sodium acetate, sodium chloride, cesium acetate, or a combination thereof. In addition, any two or more of the first agents described above may be used in combination with any of the second agents described above in the inhibitor removal process of the method provided herein; any of the first agents described above may be used in combination with any two or more of the second agents described above in the inhibitor removal process of the method provided herein; and any two or more of the first agents described above may be used in combination with any two or more of the second agents described above in the inhibitor removal process of the method provided herein.

Preferred combinations of the first agent and the second agent include: ammonium acetate and aluminum chloride, sodium acetate and aluminum chloride, cesium acetate and aluminum chloride.

In step (a), a sample, a lysate of the sample, a supernatant of the lysate or a portion of the sample, the lysate or the supernatant (collectively referred to as "sample material") may be first contacted with one or more first agents. After mixing the sample material and the one or more first agents, the resulting mixture may be separated into a solid phase and a liquid phase such as by precipitation, centrifugation, or filtration, and the liquid phase is then contacted with the one or more second agents. Preferably, no separation of solid and liquid phases occurs between contacting the sample material with the one or more first agents and contacting the resulting mixture with the one or more second agents. In other words, preferably, the mixture resulting from contacting with the one or more first agents is not centrifuged, filtrated, precipitated or otherwise treated to generate a supernatant to be further mixed with the one or more second agents.

Alternatively, a sample material may be contacted first with the one or more second agents and then with the one or more first agents. In such embodiments, the mixture of the sample material and the one or more second agents is preferably not centrifuged, filtrated, or otherwise treated to generate a supernatant to be further mixed with the one or more first agents.

Preferably, a sample material is contacted with the one or more first agents and the one or more second agents at the same time. For example, the sample material may be mixed with a composition (e.g., a solution) that comprises the one or more first agents and the one or more second agents. The concentrations of the one or more first agents and the one or more second agents as well as exemplary preferred solutions are described in detail in the "Compositions" subsection below.

The mixture of step (a) is centrifuged, filtrated, precipitated, or otherwise treated in step (b) to separate its solid phase from its liquid phase wherein the one or more second agents are primarily (more than 50%) in the solid phase. The one or more second agents form complexes with inhibitors and other contaminating materials from the sample, which complexes are precipitated out or otherwise removed from the liquid phase in step (b).

In certain embodiments, more than 60%, 70%, or 80%, preferably more than 90%, or more preferably more than 95% of the one or more second agents are removed from the liquid phase in step (b).

As used herein, the term "inhibitor" refers to any substance that interferes with a reaction involving DNA and/or RNA isolated from a sample, and has a detrimental effect on DNA and/or RNA manipulation. Inhibitors include, for example, inhibitors of an enzymatic reaction that uses DNA or RNA as a substrate and a contaminant that disrupts hybridization of DNA or RNA.

Depending on the types of samples, inhibitors may vary. For example, inhibitors in stool samples include haemoglobin and the metabolites thereof, bilirubin, bile acids and bile acid derivatives, undigested or partially digested fiber, or undigested or partially digested food, and polysaccharides.

Inhibitors from soil samples include humic substances formed when microbes degrade plant residues and are stabilized to degradation by covalent binding of their reactive sites to metal ions and clay minerals. They comprise polycyclic aromatics to which saccharides, peptides, and phenols are attached. The predominant types of humic substances in soils are humic acids and fulvic acids. Additional humic substances include humic polymers and humin.

Additional exemplary inhibitors include chitin, decomposing plant materials, organic compounds from compost, phenolics, phenolic polymers or oligomers, polyphenol, polysaccharides, and tannin.

The method provided herein is capable of substantially removing one or more inhibitors from a sample. An inhibitor is substantially removed if 20% or less, preferably 18% or less, 15% or less, 13% or less, or 10% or less, more preferably 5% or less, 3% or less, 2% or less, or 1% or less of the inhibitor from the sample remains in the liquid phase after separating the mixture that comprises the sample material, optionally a lytic reagent, and the one or more first agents and the one or more agents into a solid phase and a liquid phase.

In certain embodiments, an inhibitor inhibits PCR amplification of isolated nucleic acids and is referred to as "a PCR inhibitor." "PCR amplification" as used herein includes various types of PCR reactions, such as qPCR and RT-PCR. The removal of such an inhibitor by a particular inhibitor removal process may be evaluated by comparing certain features (e.g., Ct values) of PCR reactions using nucleic acids isolated with the inhibitor removal process with PCR reactions using nucleic acids isolated without the inhibitor removal process. The degree of reduction in Ct values between the PCR reactions may indicate the effectiveness of the inhibitor removal process in depleting PCR inhibitor(s).

3. Nucleic Acid Isolation

The liquid phase obtained in step (b) is subsequently used for isolating nucleic acids.

The term "nucleic acids" as used herein include single- or double-stranded nucleic acids and can be any DNA (e.g., genomic DNA, plasmid DNA, bacterial DNA, yeast DNA, viral DNA, plastid DNA, cosmid DNA, and mitochondrial DNA) or any RNA (e.g., rRNA, tRNA, mRNA, and snRNA).

Any methods suitable for isolating DNA, RNA, or both DNA and RNA from a solution may be used. Preferably, a nucleic acid-binding solid support is used in nucleic acid isolation. Exemplary solid support includes silica matrices, glass particles, diatomaceous earth, magnetic beads, nitrocellulose, nylon, and anion-exchange materials. The solid support may be in the form of loose particles, filters, membranes, fibers or fabrics, or lattices, and contained in a vessel, including tubes, columns, and preferably a spin column.

To facilitate or strengthen binding of nucleic acids to a solid support, a binding solution may be used. The binding solution may be added during sample lysis (e.g., after mechanical disruption of the sample in the presence of a lytic reagent) before contacting the sample material with a protein precipitating agent and an inhibitor removing agent during the inhibitor removal process. Alternatively, the binding solution may be added to the liquid phase obtained after the inhibitor removal process.

Exemplary DNA binding solution may comprise a chaotropic agent (e.g., GuSCN or GuHCl), an alcohol (e.g., ethanol or isopropanol), or both. It may further comprise a buffer substance, such as Tris HCl.

In the embodiments where both DNA and RNA are isolated from a sample, DNA isolation and RNA isolation may be performed in parallel. In other words, the liquid phase of step (b) is divided into at least two portions: one for DNA isolation, and one for RNA isolation. Preferably, DNA and RNA are isolated sequentially.

Methods for sequentially isolating DNA and RNA are known (see e.g., U.S. Pat. No. 8,889,393, WO 2004/108925). Preferably, a solid support for binding DNA and a solid support for binding RNA are used. The solid support for binding DNA may be identical to or different from the solid support for binding RNA. When an identical solid support is used for DNA and RNA isolation, differential binding of DNA and RNA to the solid support may be achieved by adjusting the component(s) and/or their concentration(s) of binding mixtures. For example, a silica spin column may be used to bind DNA first while the flow through may be mixed with ethanol, and the resulting mixture is applied to a second silica spin column to bind RNA (Triant and Whitehead, Journal of Heredity 100:246-50, 2009).

After binding to a solid phase, DNA or RNA bound to the solid phase may be washed, and subsequently eluted from the solid phase. DNA wash solution may comprise a chaotropic agent (e.g., GuHCl), an alcohol (e.g., ethanol, isopropanol), or both. It may further comprise a buffer substance (e.g., Tris HCl), a chelating agent (e.g., EDTA (ethylenediaminetetraacetic acid)), and/or a salt (e.g., NaCl). DNA elution solution may be a buffer (e.g., a Tris buffer) or water.

RNA binding solution may comprise alcohol (e.g., ethanol, isopropanol) and optionally another organic solvent (e.g., acetone). RNA wash solution may comprise one or more of the following: a buffer substance (e.g., Tris HCl and Tris base), a chelating agent (e.g., EDTA), an alcohol, and a salt (e.g., NaCl). RNA may be eluted from a solid support using DEPC-treated or other RNase-free water.

Exemplary embodiments of the method of isolating nucleic acids are described in more detail in Examples 13 and 14 below. For example, in Example 14, a soil sample is lyzed by a lytic reagent in combination with bead beating to efficiently solubilize nucleic acids and proteins from the sample. The lysate is mixed with a DNA binding solution. DNA is bound to a silica spin column and the flow through containing RNA is then combined with a solution that binds total RNA on a second silica spin column. Each spin column containing either immobilized DNA or RNA is then washed and the immobilized DNA or RNA is eluted.

The yields and purity of isolated nucleic acids may be determined using the NANODROP® ND1000 spectrophotometer (NanoDrop Technologies Inc., Wilmington, DE), the QUBIT™ dsDNA HS Assay Kit (Q32854) as well as the QUBIT™ dsDNA Br Assay Kit (Q32853) on the QUBIT™ Fluorometer (Invitrogen Co., Carlsbad, CA), QUANT-IT™ High-Sensitivity dsDNA Assay Kit (ThermoFisher), a QUANT-IT™ RNA Assay Kit. The yield of DNA may be different measured by a spectrophotometer and a fluorometer. DNA concentration measured by the NANODROP® spectrophotometer has been observed to be higher than that measured by the QUBIT™ fluorometer in some cases.

Purity of isolated DNA and RNA may be assessed by measuring the A260/A280 nm ratio, the A260/A230 nm ratio, and A340 using, for example, the NANODROP® NDIOOO spectrophotometer (NanoDrop Technologies Inc., Wilmington, DE).

Pure DNA and RNA have A260/A280 nm ratios of 1.8 and 2.0, respectively. If there is significant contamination with proteins or phenol, the A260/A280 ratio will be less than the values given above.

The A260/A230 nm ratio is a measure of contaminants that absorb at 230 nm. Pure DNA and RNA have A260/A230 nm ratios of 2.0-2.2. Significant absorption at 230 nm indicates contamination by phenolate ion, thiocyanates, and other organic compounds.

Absorption at 340 nm (i.e., A340) is usually caused by light scattering and indicates the presence of particulate matter.

DNA isolated according to a method provided herein may have one or more of the following features:

(1) Its A260/A280 is in the range of 1.6 to 2.0, preferably 1.7 to 1.9, and more preferably 1.75 to 1.85.
(2) Its A260/A230 is in the range of 1.0 to 2.5, preferably 1.5 to 2.2.
(3) Its A340 is in the range of 0 to 0.15, preferably 0 to 0.1, more preferably 0 to 0.05.

RNA isolated according to a method provided herein may have one or more of the following features:

(1) Its A260/A280 is in the range of 1.8 to 2.2, preferably 1.9 to 2.1, and more preferably 1.95 to 2.05.
(2) Its A260/A230 is in the range of 1.0 to 2.5, preferably 1.5 to 2.2.
(3) Its A340 is in the range of 0 to 0.15, preferably 0 to 0.1, more preferably 0 to 0.05.

The integrity of isolated DNA may be assessed by visualizing extracted DNA on an agarose gel. The integrity of isolated RNA may also be assessed by visualizing extracted RNA using gel electrophoresis.

The isolated DNA may be analyzed or used in any application, including PCR, qPCR, RT-PCR, rolling circle replication, ligase-chain reaction, sequencing (e.g., next generation sequencing, southern, dot, and slot blot analyses, DNA methylation analysis, mass spectrometry, and electrophoresis.

The isolated RNA may be analyzed or used in any application, such as RT-PCR, real-time RT-PCR, differential display, cDNA synthesis, Northern, dot, and slot blot analyses, and microarray analysis.

B. Compositions

In a related aspect, the present disclosure provides a composition useful in removing inhibitors during nucleic acid isolation from a sample. The composition comprises, consists essentially of, or consists of one or more first agents selected from ammonium acetate, ammonium sulfate, potassium acetate, sodium acetate, sodium chloride, cesium acetate, and combinations thereof; one or more second agents selected from aluminum chloride, erbium (III) acetate, erbium (III) chloride, holmium chloride, hafnium (IV) chloride, zirconium (IV) chloride, and combinations thereof, and optionally water.

First agents, second agents and combinations of the first agents and the second agents are as described above in section "II. Nucleic Acid Isolation," subsection "A. Methods" above.

The composition is preferably an aqueous solution. In such a case, the total concentration of the one or more first agents in the solution may be in the range of 0.5 to 10M, such as 0.5 to 2.5M, 2.5 to 5M, 5 to 7.5M, 7.5 to 10M, 0.5 to 5M, 0.5 to 7.5M, 0.5 to 10M, 2.5 to 7.5M, 2.5 to 10M, 5 to 10M, preferably 0.5 to 5M, 0.5 to 7.5M, 2.5 to 5M, 2.5 to 7.5M, 1 to 8M or 1.5 to 7.5M. If multiple first agents are present in the solution, the concentration of an individual first agent in the solution may be in the range of 0.1 to 9.5M, such as 0.1 to 0.5M, 0.5 to 2.5M, 2.5 to 5M, 5 to 7.5M, 7.5 to 9.5M, 0.1 to 2.5M, 0.1 to 5M, 0.1 to 7.5M, 0.5 to 5M, 0.5 to 7.5M, 0.5 to 9.5M, 2.5 to 7.5M, 2.5 to 9.5M, 5 to 9.5M, preferably 0.1 to 5M, 0.5 to 7.5M, 2.5 to 5M, 2.5 to 7.5M, 1 to 8M or 1.5 to 7.5M. The total concentration of the one or more second agents in the solution may be in the range of 10 to 500 mM, such as 10 to 100 mM, 100 to 200 mM, 200 to 300 mM, 300 to 400 mM, 400 to 500 mM, 100 to 300 mM, 100 to 400 mM, 100 to 500 mM, 200 to 400 mM, 200 to 500 mM, 300 to 500 mM, preferably 10 to 200 mM, 10 to 500 mM, 50 to 200 mM, 50 to 500 mM or 75 to 150 mM. If multiple second agents are present in the solution, the concentration of an individual second agent in the solution may be in the range of 1 to 450 mM, such as 1 to 10 mM, 10 to 100 mM, 100 to 200 mM, 200 to 300 mM, 300 to 400 mM, 400 to 450 mM, 1 to 200 mM, 1 to 300 mM, 1 to 400 mM, 1 to 450 mM, 100 to 300 mM, 100 to 400 mM, 100 to 450 mM, 200 to 400 mM, 200 to 450 mM, 300 to 450 mM, preferably 1 to 200 mM, 10 to 450 mM, 50 to 200 mM, 50 to 450 mM or 75 to 150 mM.

Exemplary preferred solutions that comprise a first agent and a second agent include:

(1) a solution containing 1 to 8M (preferably 2.5 to 5M) ammonium acetate and 20 to 200 mM aluminum chloride;
(2) a solution containing 1 to 10M (preferably 1 to 8M) sodium acetate and 20 to 200 mM aluminum chloride;
(3) a solution containing 1 to 8M (preferably 1 to 5M) cesium acetate and 20 to 200 mM aluminum chloride;
(4) a solution containing 1 to 8M (preferably 2.5 to 5M) ammonium acetate and 20 to 200 mM erbium (III) acetate;
(5) a solution containing 1 to 10M (preferably 1 to 8M) sodium acetate and 20 to 200 mM erbium (III) acetate;
(6) a solution containing 1 to 8M (preferably 1 to 5M) cesium acetate and 20 to 200 mM erbium (III) acetate;
(7) a solution containing 1 to 8M (preferably 2.5 to 5M) ammonium acetate and 20 to 200 mM erbium (III) chloride;
(8) a solution containing 1 to 10M (preferably 1 to 8M) sodium acetate and 20 to 200 mM erbium (III) chloride;
(9) a solution containing 1 to 8M (preferably 1 to 5M) cesium acetate and 20 to 200 mM erbium (III) chloride;
(10) a solution containing 1 to 8M (preferably 2.5 to 5M) ammonium acetate and 20 to 200 mM holmium chloride;
(11) a solution containing 1 to 10M (preferably 1 to 8M) sodium acetate and 20 to 200 mM holmium chloride; and
(12) a solution containing 1 to 8M (preferably 1 to 5M) cesium acetate and 20 to 200 mM holmium chloride.

Alternatively, the composition may be in solid form. In such a case, the composition comprises, consists essentially of, or consists of one or more first agents and one or more second agents so that when an appropriate amount of water is added to the composition, the resulting solution has the concentrations of the one or more first agents and the one or more second agents as described above in the case where the composition is already a solution. The water that is added may also result from the water in the sample, i.e., the combination of salts may be added directly to the aqueous sample material.

In a related aspect, the present disclosure provides the use of the above-described compositions in isolating nucleic acids from a sample.

C. Kits

In another aspect, the present disclosure provides a kit for isolating nucleic acids from a sample. The kit comprises a composition comprising one or more first agents and one or more second agents as described in section "II. Nucleic Acid Isolation," subsection "Compositions" above. Alternatively, the kit comprises one or more first agents and one or more second agents provided separately.

The kit may further comprise one or more of the following components:

a lytic reagent,
a homogenizing material,
a nucleic acid-binding solid support,
a DNA binding solution,
a DNA wash solution,
a DNA elution solution,
a RNA binding solution,
a RNA wash solution,
a RNA elution solution, and
one or more vessels or containers (e.g., collection tubes).

The lytic reagent is preferably a lytic reagent comprising, consisting essentially of, or consisting of a phosphate and a relatively mild chaotropic agent as described in section "I. Sample Lysis" above.

The homogenizing material refers to a substance useful in homogenizing a sample such as beads, preferably high density beads for mechanically disrupting a sample as described above in section "I. Sample Lysis," subsection "C. Lysis process" above.

The other optional kit components are as described in section "I. Sample Lysis," subsection "D. Kits" above.

In a related aspect, the present disclosure provides the use of the above-described kit in isolating nucleic acids from a sample.

EXAMPLES

The following reagents are referred to in the examples below:

Lytic Reagent I: 1M NaSCN, 0.2M Na2HPO4.

Lytic Reagent II: 0.09 M Guanidine Thiocyanate, 0.13 M Na2HPO4, 0.006 M NaCl, 1.76M ammonium acetate, 0.25% SDS, 0.10% Antifoam A.

Lysis solution I: 0.18M Na2HPO4, 0.12M GuSCN, pH 8.8-9.2.

Lysis solution II: 0.1M NaCl, 0.5 M Tris Base, 4% SDS (0.14 M), pH 10.75-11.25.

DNA binding solution I: containing a chaotropic agent.

DNA binding solution II: containing a chaotropic agent, buffer and isopropanol.

DNA binding solution III: containing ethanol.

DNA binding solution IV: containing a chaotropic agent, a buffer base, and ethanol.

DNA wash solution I: containing a chaotropic agent, buffer, and isopropanol, and ethanol.

DNA wash solution II: containing buffer, a chelating agent, a salt, and ethanol.

DNA elution solution: containing buffer with a slightly basic pH.

RNA binding solution: containing acetone and ethanol.

RNA wash solution: containing buffer, a chelating agent, a salt and alcohol.

Protein binding solution: containing a salt and buffer with an acidic pH.

Protein wash solution: containing ethanol.

Protein elution solution: containing buffer with a slightly basic pH and a detergent.

Example 1

Effects of Lytic Reagents with or without Inhibitor Removal on DNA Isolation from Stool Samples This example examines the effects of different lytic reagents with or without inhibitor removal on DNA isolation from stool samples.

Four different experiments (A, B, C, and D) were performed as shown in the table below. A and B used an exemplary lytic reagent ("lytic reagent I") of the present disclosure while C and D used an existing lytic reagent ("lytic reagent II"). A and C did not perform inhibitor removal while B and D did.

| | | A | B | C | D |
|---|---|---|---|---|---|
| Input | 0.2 g frozen dog stool | X | X | X | X |
| Lysis, 650 μl | Lytic reagent I | X | X | | |
| | Lytic reagent II | | | X | X |
| | 100 μl phenol | | | X | X |
| | 6.5 μl beta-mercaptoethanol (beta-ME) | X | X | X | X |
| | 6.5 μl Protease Inhibitors | X | X | | |
| DNA Bind (350 μl) | DNA binding solution | X | X | | |
| Inhibitor Removal (150 μl) | 52 mM AASD | | X | | |
| | 0.12M AASD | | | | X |
| DNA Bind (350 μl) | DNA binding solution | | | X | X |
| DNA Wash | DNA wash solution I | X | X | X | X |
| | DNA wash solution II | X | X | X | X |
| DNA Elute | DNA elute solution | X | X | X | X |

The yields and purity of isolated DNA are shown in the tables below:

| Quant-iT dsDNA | | |
|---|---|---|
| Sample | Sample Concentration | Average |
| A | 130 ug/mL | |
| A | 111 ug/mL | |
| A | 131 ug/mL | |
| A | 128 ug/mL | |
| A | 116 ug/mL | 123.2 |
| B | 85 ug/mL | |
| B | 78.6 ug/mL | |
| B | 79.7 ug/mL | |
| B | 93 ug/mL | |
| B | 85.3 ug/mL | 84.32 |
| C | 68.6 ug/mL | |
| C | 69.4 ug/mL | |
| C | 66.5 ug/mL | |
| C | 60.6 ug/mL | |
| C | 61.4 ug/mL | 65.3 |
| D | 38.6 ug/mL | |
| D | 39.1 ug/mL | |
| D | 40.6 ug/mL | |
| D | 40.9 ug/mL | |
| D | 41.8 ug/mL | 40.2 |

The above results were obtained using the QUANT-IT™ dsDNA Assay Kit (ThermoFisher Scientific) according to the provider's instructions.

NanoDrop

| Sample | DNA(ng/uL) | A260/A280 | A260/A230 | A340 |
|---|---|---|---|---|
| A | 167.176 | 1.826 | 1.016 | 0.096 |
| A | 152.183 | 1.821 | 1.153 | 0.109 |
| A | 166.272 | 1.81 | 1.431 | 0.125 |
| A | 161.637 | 1.822 | 1.393 | 0.091 |
| A | 160.319 | 1.816 | 1.406 | 0.109 |
| B | 111.448 | 1.832 | 0.799 | 0.046 |
| B | 110.381 | 1.831 | 0.64 | 0.074 |
| B | 112.97 | 1.81 | 1.734 | 0.051 |
| B | 113.903 | 1.843 | 1.53 | 0.075 |
| B | 108.207 | 1.828 | 0.956 | 0.079 |
| C | 101.056 | 1.782 | 0.779 | 0.077 |
| C | 97.665 | 1.801 | 1.447 | 0.104 |
| Sample | DNA(ng/uL) | A260/A280 | A260/A230 | A340 |
| C | 98.104 | 1.788 | 1.666 | 0.113 |
| C | 97.556 | 1.793 | 1.267 | 0.078 |
| C | 94.579 | 1.799 | 1.429 | 0.121 |
| D | 58.715 | 1.767 | 0.314 | −0.321 |
| D | 55.321 | 1.802 | 0.593 | 0.039 |
| D | 60.959 | 1.753 | 0.226 | 0.051 |
| D | 57.62 | 1.799 | 0.324 | 0.07 |
| D | 58.641 | 1.782 | 0.662 | 0.054 |

The above results were obtained using THERMOSCIENTIFIC™ NANODROP™ ND-1000 spectrophotomer (ThermoFisher Scientific) according to the provider's instructions.

The gel electrophoresis of the isolated DNA is shown in FIG. 1.

The results show that compared to lytic reagent II, lytic reagent I extracted and solubilized much more DNA. Without inhibitor removal, the difference in DNA yield between the two lysis methods was 47%. With inhibitor removal, the difference was 52%.

Example 2

Effects of Titration of Ammonium Acetate on DNA, RNA and Protein Isolation from Stool Samples This example examines the effects of various concentrations of ammonium acetate on DNA, RNA and protein isolation from stool samples.

Dog stool was previously collected and immediately frozen. The aliquot used for this experiment had been thawed once. Bead beating was in the mixed zirconium bead tubes (1.2 g 0.1 mm+1.2 g 0.5 mm) for 10 minutes on the vortex at maximum setting. After lysis and the addition of DNA binding solution, all the supernatants were pooled. About 800 μl was recovered from each tube, but 750 μl was re-aliquoted for the inhibitor removal step. All the concentrations of $NH_4OAc$ are the concentrations after being combined with aluminum ammonium sulfate dodecahydrate (AASD).

| | | A | B | C | D | E | F |
|---|---|---|---|---|---|---|---|
| Input | 0.2 g frozen dog stool | X | X | X | X | X | X |
| Lysis, 650 μl | 1M NaSCN + 0.2M $Na_2HPO_4$ | X | X | X | X | X | X |
| | 6.5 μl beta-ME | X | X | X | X | X | X |
| | 6.5 μl Protease Inhibitors | X | X | X | X | X | X |
| DNA Bind (350 μl) | DNA binding solution | X | X | X | X | X | X |
| Inhibitor Removal (150 μl) | Water | X | | | | | |
| | 0.06M AASD | | X | X | X | X | X |
| | 3.75M $NH_4OAc$ | | X | | | | |
| | 0.9375M $NH_4OAc$ | | | X | | | |
| | 0.46875M $NH_4OAc$ | | | | X | | |
| | 0.234375M $NH_4OAc$ | | | | | X | |
| DNA Wash | DNA wash solution I | X | X | X | X | X | X |
| | DNA wash solution II | X | X | X | X | X | X |
| DNA Elute | DNA elution solution | X | X | X | X | X | X |
| RNA Bind (750 μl) | RNA binding solution I | X | X | X | X | X | X |
| RNA Wash | RNA wash solution | X | X | X | X | X | X |
| | Ethanol | X | X | X | X | X | X |
| RNA Elute | RNase-free water | X | X | X | X | X | X |
| Protein Bind (1400 μl) | Protein binding solution | X | X | X | X | X | X |
| Protein Wash | Protein wash solution | X | X | X | X | X | X |
| Protein Elute | Protein elution solution | X | X | X | X | X | X |

The yields and purity of isolated nucleic acids are shown in the tables below:

NanoDrops

| Sample | DNA(ng/uL) | A260/A280 | A260/A230 | A340 |
|---|---|---|---|---|
| A | 104.416 | 1.825 | 0.438 | 0.007 |
| A | 95.522 | 1.831 | 1.109 | 0.043 |
| B | 85.73 | 1.839 | 0.517 | 0.025 |
| B | 101.538 | 1.82 | 0.442 | 0.019 |
| C | 53.212 | 1.837 | 0.169 | 0.038 |
| C | 46.831 | 1.862 | 0.568 | −0.039 |
| D | 90.398 | 1.874 | 0.145 | 0.119 |
| D | 95.833 | 1.83 | 0.683 | 0.023 |
| E | 100.071 | 1.823 | 1.028 | 0.021 |
| E | 103.32 | 1.827 | 1.514 | −0.008 |
| F | 103.579 | 1.82 | 0.904 | 0.014 |
| F | 99.634 | 1.974 | 0.497 | 21.406 |
| Sample | RNA(ng/uL) | A260/A280 | A260/A230 | A340 |
| A | 278.767 | 2.052 | 0.986 | 21.997 |
| A | 316.745 | 1.983 | 1.059 | 0.551 |
| B | 344.048 | 1.996 | 1.137 | 0.471 |
| B | 307.839 | 1.993 | 0.971 | 0.407 |
| C | 394.183 | 2.001 | 1.21 | 0.582 |
| C | 389.246 | 2.003 | 1.18 | 0.649 |
| D | 364.583 | 1.995 | 1.163 | 0.991 |
| D | 314.102 | 1.995 | 1.066 | 0.524 |
| E | 363.972 | 1.998 | 0.69 | 0.602 |
| E | 329.715 | 2.009 | 1.024 | 0.502 |
| F | 365.367 | 2.01 | 1.086 | 0.506 |
| F | 335.324 | 2 | 1.095 | 0.426 |

DNA Qubits

| Sample | DNA Concentration | Average |
|---|---|---|
| A | 69.9 ug/mL | |
| A | 67.3 ug/mL | 68.6 |
| B | 59 ug/mL | |
| B | 65.3 ug/mL | 62.2 |
| C | 30 ug/mL | |
| C | 27.3 ug/mL | 28.7 |
| D | 54.7 ug/mL | |
| D | 63 ug/mL | 58.9 |
| E | 70 ug/mL | |
| E | 71.8 ug/mL | 70.9 |
| F | 72.6 ug/mL | |
| F | 79.6 ug/mL | 76.1 |

The results from the above table were obtained using INVITROGEN™ QUBIT™ fluorometer (Invitrogen) according to the provider's instructions.

Figure 2:
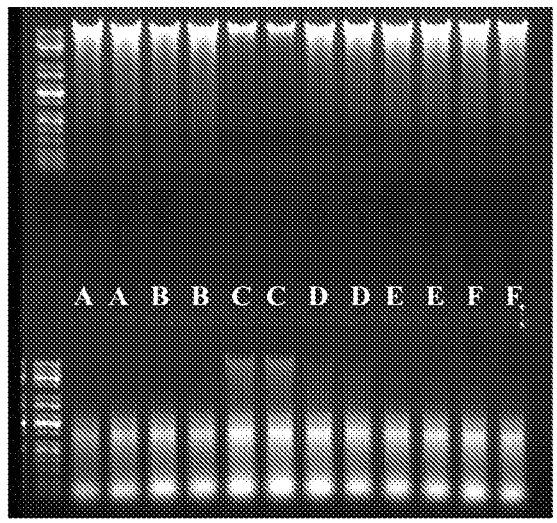
FIG. 2 shows gel electrophoresis of DNA (upper panel), RNA (middle panel), and proteins (lower panel) isolated according to Example 2.
Figure 2:
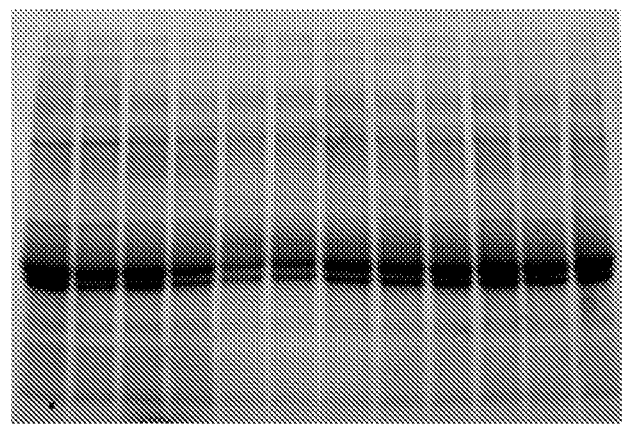

The gel electrophoresis of the isolated DNA, RNA and proteins is shown in FIG. 2, upper, middle and lower panels, respectively.

The results show that 3.75M ammonium acetate caused substantial DNA loss and a reduction in DNA binding. DNA, RNA and protein isolation were all improved to match or exceed the control (3.75M ammonium acetate) when ammonium acetate was used at or lower than 0.9375M. The best yields for all the nucleic acid and protein with A260/A230 at least 1.0 was E (0.234375M ammonium acetate) for DNA and D (0.46875M ammonium acetate) for RNA.

Example 3

DNA Isolation from Soil Samples

This example examines the effects of different lysis and/or inhibitor removal methods on DNA isolation from soil samples.

DNA isolation was performed as shown in the table below. All samples were done in quadruplicate except control (sample 5).

| | | 1 | 2 | 3 | 4 | 5 |
|---|---|---|---|---|---|---|
| Input | Garden soil (VVG), 0.25 g | x | x | x | x | x |
| Lysis | Zymo ZR BashingBead Lysis Tubes | x | x | x | | |
| | 0.7 mm garnet beads (QIAGEN) | | | | x | x |
| | PowerLyzer (2,500 RPM; 45 secs) | x | | | | |
| | PowerLyzer (1,800 RPM; 5 min) | | x | | | |
| | Vortex | | | x | x | x |
| | 0.18M $Na_2HPO_4$, 810 µl | x | x | x | x | |
| | Lysis solution I, 750 µl | | | | | x |
| | Lysis solution II, 60 µl | | | | | x |
| Inhibitor removal | 3.75M $NH_4OAc$, 0.096M AASD; 250 µl | x | x | x | x | |
| | 3.8M $NH_4OAc$, 250 µl | | | | | x |
| | 0.12M AASD, 200 µl | | | | | x |
| DNA Bind | DNA binding solution II, 1200 µl | x | x | x | x | x |
| DNA Wash | DNA wash solution II, 500 µl | x | x | x | x | x |
| DNA Elute | DNA elution solution, 100 µl | x | x | x | x | x |

Garden soil (VVG): a very rich garden soil that contains a high concentration of PCR-inhibitory compounds.

The yields and purity of isolated DNA are shown in the tables below.

| Sample | (ng/uL) | A260/ A280 | A260/ A230 | A260 | A280 | Nucleic Acid Factor | Baseline Correction (nm) | Baseline Absorbance |
|---|---|---|---|---|---|---|---|---|
| 1 | 73.938 | 1.843 | 1.79 | 1.479 | 0.802 | 50 | 340 | 0.088 |
| 1 | 81.278 | 1.865 | 1.784 | 1.626 | 0.871 | 50 | 340 | 0.089 |
| 1 | 65.916 | 1.807 | 1.845 | 1.318 | 0.73 | 50 | 340 | 0.078 |
| 1 | 87.499 | 1.847 | 1.846 | 1.75 | 0.947 | 50 | 340 | 0.123 |
| 2 | 69.12 | 1.81 | 1.843 | 1.382 | 0.764 | 50 | 340 | 0.154 |
| 2 | 83.089 | 1.866 | 1.934 | 1.662 | 0.891 | 50 | 340 | 0.102 |
| 2 | 92.904 | 1.854 | 1.928 | 1.858 | 1.002 | 50 | 340 | 0.158 |
| 2 | 81.157 | 1.852 | 1.914 | 1.623 | 0.877 | 50 | 340 | 0.1 |
| 3 | 74.565 | 1.861 | 1.899 | 1.491 | 0.801 | 50 | 340 | 0.048 |
| 3 | 71.624 | 1.86 | 1.878 | 1.432 | 0.77 | 50 | 340 | 0.084 |
| 3 | 66.018 | 1.847 | 1.937 | 1.32 | 0.715 | 50 | 340 | 0.061 |
| 3 | 81.778 | 1.879 | 2.052 | 1.636 | 0.871 | 50 | 340 | 0.093 |
| 4 | 59.638 | 1.859 | 1.835 | 1.193 | 0.642 | 50 | 340 | 0.098 |
| 4 | 53.228 | 1.823 | 1.81 | 1.065 | 0.584 | 50 | 340 | 0.094 |
| 4 | 55.753 | 1.835 | 1.816 | 1.115 | 0.608 | 50 | 340 | 0.101 |
| 4 | 60.488 | 1.852 | 1.905 | 1.21 | 0.653 | 50 | 340 | 0.104 |
| 5 | 23.355 | 1.844 | 1.425 | 0.467 | 0.253 | 50 | 340 | 0.108 |
| 5 | 21.532 | 1.867 | 1.095 | 0.431 | 0.231 | 50 | 340 | 0.094 |

Average DNA Yields

| | (ng/uL) | A260/A280 | A260/A230 | 340 |
|---|---|---|---|---|
| 1 | 77.158 | 1.841 | 1.816 | 0.095 |
| 2 | 81.568 | 1.846 | 1.905 | 0.129 |
| 3 | 73.496 | 1.862 | 1.942 | 0.072 |
| 4 | 57.277 | 1.842 | 1.842 | 0.099 |
| 5 | 22.444 | 1.856 | 1.260 | 0.101 |

Figure 3:
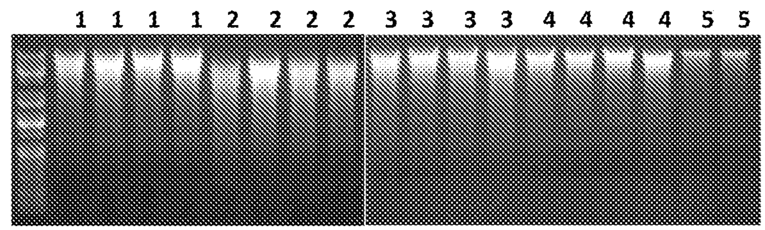
FIG. 3 shows gel electrophoresis of DNA isolated according to Example 3.

The gel electrophoresis of the isolated DNA is shown in FIG. 3.

The results show that Sample 1 and 3 conditions produced the highest DNA yield with the least amount of DNA shearing. The PowerLyzer did not dramatically improve DNA yields but it saved the time normally spent on bead beating. Sample 2 produced the highest yields, but the DNA was in smaller fragments. The purity of these samples was very good because the lysate was almost black prior to inhibitor removal. Sample 4 used garnet beads. The zirconium bead tube outperformed these samples by 20 ng/µl (2 µg). Sample 5 was the traditional protocol and used as a control. This experiment shows that DNA yields could be improved by 250%.

Example 4

Effects on Different Lysis Buffer on DNA Isolation from Soil Samples

This example examines the effects of different lysis buffer on DNA isolation from soil samples.

DNA isolation was performed as shown in the table below. All samples were done in duplicate. No samples were pooled at any point.

| | | 1 | 2 | 3 | 4 | 5 |
|---|---|---|---|---|---|---|
| Input | Garden soil (VVG), 0.25 g | x | x | x | x | x |
| Lysis | Zymo ZR BashingBead Lysis Tubes | x | x | x | x | |
| | 0.7 mm garnet beads (QIAGEN) | | | | | x |
| | 1M NaSCN, 0.18M $Na_2HPO_4$, 810 µl | x | | | | |
| | 1M $NH_4SCN$, 0.18M $Na_2HPO_4$, 810 µl | | x | | | |

-continued

| | | 1 | 2 | 3 | 4 | 5 |
|---|---|---|---|---|---|---|
| | 0.1M $Na_2CO_3$, 0.18M $Na_2HPO_4$, 810 µl | | | x | | |
| | 0.18M $Na_2HPO_4$, 810 µl | | | | x | |
| | Lysis solution I, 750 µl | | | | | x |
| | Lysis solution II, 60 µl | | | | | x |
| Inhibitor Removal | 3.75M $NH_4OAc$, 0.096M AASD; 250 µl | x | x | x | x | |
| | 3.8M $NH_4OAc$, 250 µl | | | | | x |
| | 0.12M AASD, 200 µl | | | | | x |
| DNA Bind | DNA binding solution II, 1200 µl | x | | x | x | x |
| | DNA binding solution III, 700 µl | | x | | | |
| DNA Wash | DNA wash solution II, 500 µl | x | x | x | x | x |
| DNA Elute | DNA elution solution, 100 µl | x | x | x | x | x |

The yields and purity of isolated DNA are shown in the tables below.

| Sample | (ng/uL) | A260/ A280 | A260/ A230 | A260 | A280 | Nucleic Acid Factor | Baseline Correction (nm) | Baseline Absorbance |
|---|---|---|---|---|---|---|---|---|
| 1 | 70.849 | 1.842 | 1.221 | 1.417 | 0.769 | 50 | 340 | 0.067 |
| 1 | 68.953 | 1.852 | 1.657 | 1.379 | 0.745 | 50 | 340 | 0.093 |
| 2 | 167.884 | 1.624 | 0.529 | 3.358 | 2.068 | 50 | 340 | 1.736 |
| 2 | 173.805 | 1.586 | 0.615 | 3.476 | 2.192 | 50 | 340 | 2.008 |
| 3 | 51.361 | 1.789 | 1.577 | 1.027 | 0.574 | 50 | 340 | 0.132 |
| 3 | 58.395 | 1.813 | 1.683 | 1.168 | 0.644 | 50 | 340 | 0.035 |
| 4 | 62.15 | 1.866 | 1.85 | 1.243 | 0.666 | 50 | 340 | 0.076 |
| 4 | 66.362 | 1.875 | 2.043 | 1.327 | 0.708 | 50 | 340 | 0.071 |
| 5 | 18.29 | 1.866 | 1.285 | 0.366 | 0.196 | 50 | 340 | 0.113 |
| 5 | 18.105 | 1.858 | 1.163 | 0.362 | 0.195 | 50 | 340 | 0.09 |

Figure 4:
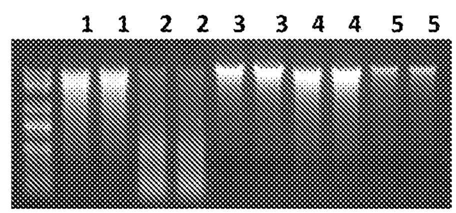
FIG. 4 shows gel electrophoresis of DNA isolated according to Example 4.

The gel electrophoresis of the isolated DNA is shown in FIG. 4.

The results show that Sample 1 DNA appeared to have higher DNA yields than the phosphate only control (Sample 4), suggesting that adding NaSCN to the phosphate only lysis buffer improved DNA yield. Sample 2 DNA yields were difficult to determine via gel and nanodrop because the ethanol in DNA binding solution III caused RNA to bind as well. Sample 3 produced quality DNA.

Example 5

Effects on Different Lysis Buffer on DNA Isolation from Stool Samples

This example examines the effects of different lysis on DNA isolation from stool samples.

All samples were done in duplicate and processed in two parts as shown in the tables below. All samples were pooled after lysis. 540 uL was distributed to each sample.

Part 1

| | | 1 | 2 | 3 | 4 | 5 |
|---|---|---|---|---|---|---|
| Input | Dog stool, 0.2 g | x | x | x | x | x |
| Lysis | 1.2 g 0.1 mm + 1.2 g 0.5 mm beads (MOBIO) | x | x | x | x | x |
| | 0.18M $Na_2HPO_4$, 810 µl | x | x | x | x | |
| | 1M NaSCN, 0.18M $Na_2HPO_4$, 810 µl | | | | | x |
| Inhibitor Removal | 3.75M $NH_4OAc$, 0.096M AASD; 250 µl | x | x | | | |
| DNA Bind | DNA binding solution I, 500 µl | x | | x | | x |
| | DNA binding solution II, 1200 µl | | x | | x | |
| DNA Wash | DNA wash solution I, 650 µl | x | | x | | x |
| | DNA wash solution II, 500 µl | x | x | x | x | x |
| DNA Elute | DNA elution solution, 100 µl | x | x | x | x | x |

Part 2

| | | 6 | 7 | 8 |
|---|---|---|---|---|
| Input | Dog stool, 0.2 g | x | x | |
| | BT 1 from P1 | | | x |
| Lysis | 1.2 g 0.1 mm + 1.2 g 0.5 mm beads (MOBIO) | | x | |
| | 0.7 mm garnet beads (QIAGEN) | x | | |
| | Lysis solution I, 750 µl | x | | |
| | Lysis solution II, 60 µl | x | | |
| | 1M NaSCN + 0.18M $Na_2HPO_4$, 810 µl | | x | x |
| DNA Bind | DNA binding solution II, 1200 µl | x | | |
| | DNA binding solution I, 500 µl | | x | x |
| DNA Wash | DNA wash solution I, 650 µl | | x | x |
| | DNA wash solution II, 500 µl | x | x | x |
| DNA Elute | DNA elution solution, 100 µl | x | x | x |

"BT 1 from P1" refers to the bead tube composition (including buffer) in Group 1 (1.2 g 0.1 mm and 1.2 g 0.5 mm beads+0.18 M phosphate). This same bead tube was used in Group 8 but, after lysis and removal of the supernatant, 1 M NaSCN+0.18 M $Na_2HPO_4$ was added back into the bead tube to check if DNA—if released during the lysis step—could be solubilized.

Figure 5:
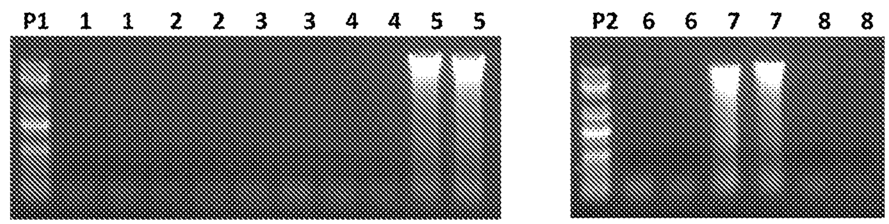
FIG. 5 shows gel electrophoresis of DNA isolated according to Example 5.

The gel electrophoresis of isolated DNA is shown in FIG. 5.

The results show that NaSCN appeared to be required for microbial lysis in stool samples. Specifically, DNA was isolated from Samples 5 and 7 that contained NaSCN in addition to phosphate in the lysis solution while little DNA was isolated from the other samples that did not contain NaSCN in the lysis solution.

Example 6

Comparison of DNA Isolation from Stool Samples Among Different Kits

This example compares DNA isolation from stool samples among different commercially available kits (tests 1 to 3) and an exemplary method ("New Technique," test 4) of the present disclosure.

All samples were done in triplicate. Each kit protocol was followed. Bead beating was standardized across all kits. Bead tubes were homogenized at max speed for 10 minutes.

| Manufacturer | Kit | Cat # |
|---|---|---|
| Zymo Research | ZymoBIOMICSDNA Miniprep Kit | D4300 |
| ThermoFischer | PureLink Microbiome DNA Purification Kit | A29790 |
| MO BIO | PowerFecal DNA Isolation Kit | 12830-50 |

| | 1 | 2 | 3 | 4 |
|---|---|---|---|---|
| Input | O2, 0.2 g | A | A | A | A |
| | O5, 0.2 g | B | B | B | B |
| | Y2, 0.2 g | C | C | C | C |
| | ZymoBIOMICSDNA Miniprep Kit | x | | | |
| | PureLink Microbiome DNA Purification Kit | | x | | |
| | PowerFecal DNA Isolation Kit | | | x | |
| Lysis | 1.2 g 0.1 mm + 1.2 g 0.5 mm beads (MOBIO) | | | | x |
| | 1M NaSCN, 0.18M $Na_2HPO_4$, 800 µl | | | | x |
| Bead Beating | Vortex adapter for 10 mins @ max speed | x | x | x | x |
| Inhibitor Removal | 3.75M $NH_4OAc$, 0.096M AASD; 200 µl | | | | x |
| DNA Bind | DNA binding solution I, 450 µl | | | | x |
| | Transfer spin filter to new collection tube | | | | x |
| DNA Wash | DNA wash solution I, 650 µl | | | | x |
| | DNA wash solution II, 650 µl | | | | x |
| DNA Elute | DNA elution solution, 100 µl | | | | x |

The designations "O" and "Y" correspond to human stool samples from old, "O" vs. young "Y" donors. "Old" donors were 65 years old and above; "young" donors were under 50 years old.

ZymoBIOMICS DNA Miniprep Kit samples A clogged the Zymo-Spin IV Spin Filter. The samples were split over 2 spin filters and recombined the lysate after centrifugation.

Figure 6A:
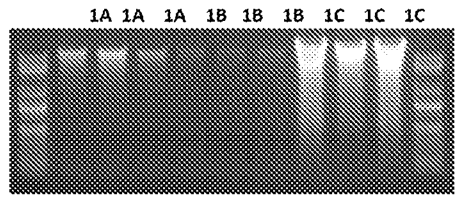
FIG. 6A shows gel electrophoresis of DNA isolated using ZymoBIOMICS DNA Miniprep Kit.
Figure 6B:
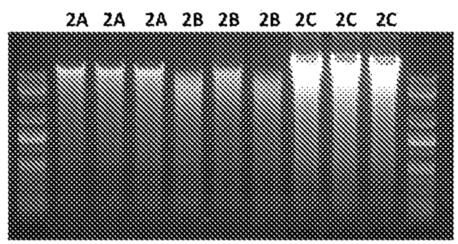
FIG. 6B shows gel electrophoresis of DNA isolated using PureLink Microbiome DNA Purification Kit.
Figure 6C:
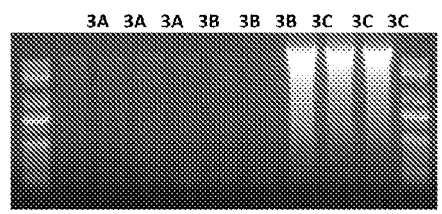
FIG. 6C shows gel electrophoresis of DNA isolated using PowerFecal DNA Isolation Kit.
Figure 6D:
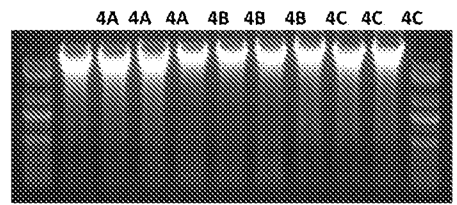
FIG. 6D shows gel electrophoresis of DNA isolated using an exemplary method ("New Technique") of the present disclosure.

The gel electrophoresis of isolated DNA is shown in FIG. 6A (ZymoBIOMICS DNA Miniprep Kit), FIG. 6B (PureLink Microbiome DNA Purification Kit), FIG. 6C (MO BIO Power Soil), and FIG. 6D (New Technique).

Figure 6E:
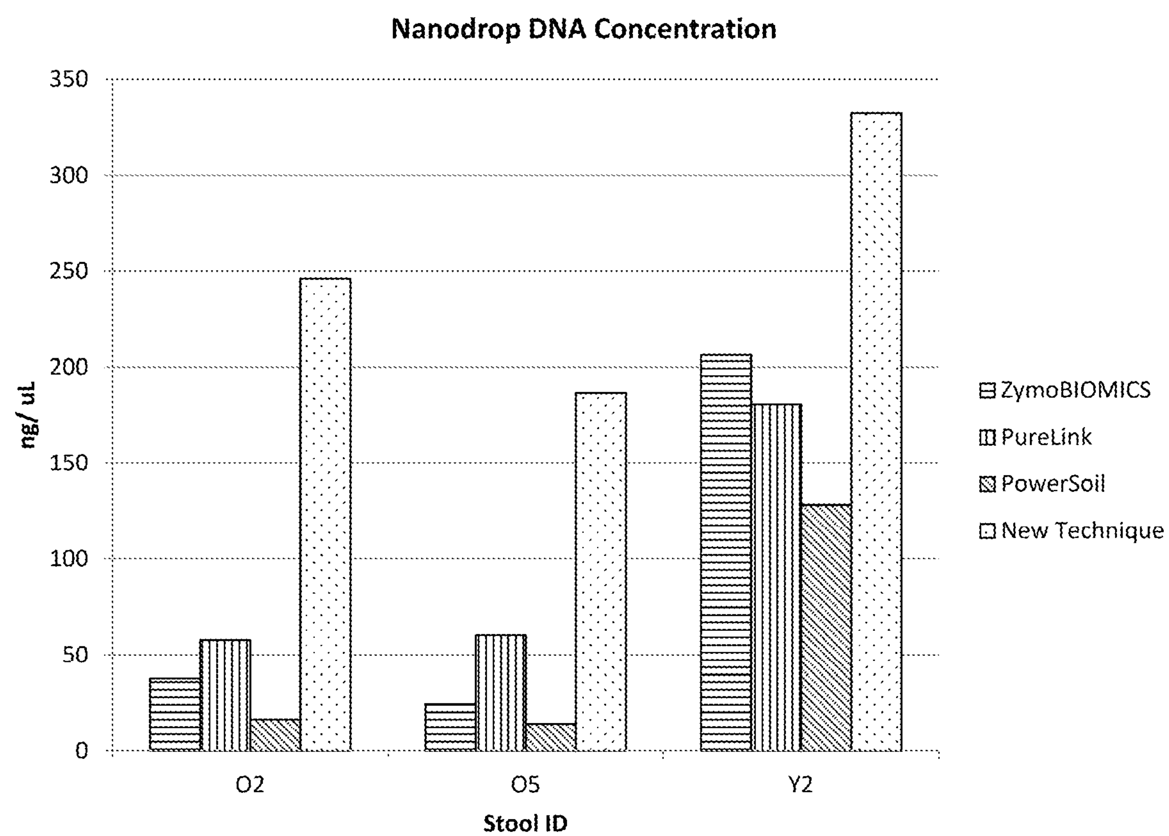
FIG. 6E is a graph that shows concentrations of DNA isolated from fecal samples using different kits measured using Nanodrop.

The concentrations of isolated DNA by different kits measured by NanoDrop are shown in the table below and in FIG. 6E.

| | ZR Soil Microbe DNA | PureLink Microbiome DNA | PowerSoil DNA Isolation Kit | New Technique |
|---|---|---|---|---|
| O2 | 37.69 | 57.82 | 16.42 | 246.10 |
| O5 | 24.33 | 60.33 | 14.07 | 186.51 |
| Y2 | 206.41 | 180.55 | 128.17 | 332.55 |

*** averages use corrected ng/uL

Figure 6F:
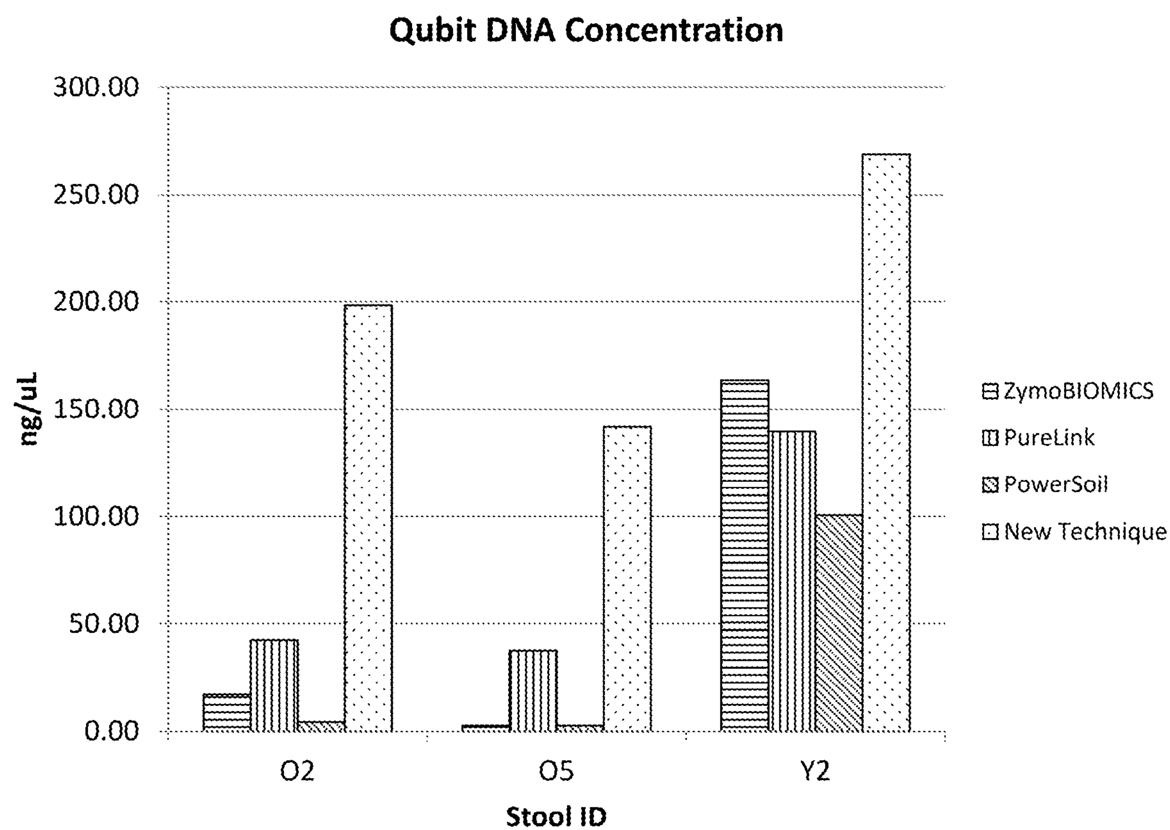
FIG. 6F is a graph that shows concentrations of DNA isolated from fecal samples using different kits measured using Qubit.

The purity and concentrations of isolated DNA by different kits measured by Qubit are shown in the tables below and in FIG. 6F.

| | O2 | | | | O5 | | | | Y2 | | | |
|---|---|---|---|---|---|---|---|---|---|---|---|---|
| | 260/280 | sd | 260/230 | sd | 260/280 | sd | 260/230 | sd | 260/280 | sd | 260/230 | sd |
| Zymo BIOMICS | 1.513 | 0.029 | 0.425 | 0.340 | 1.330 | 0.062 | 0.402 | 0.118 | 1.755 | 0.037 | 1.308 | 0.694 |
| PureLink | 1.777 | 0.003 | 1.411 | 0.027 | 1.768 | 0.040 | 1.431 | 0.203 | 1.853 | 0.004 | 2.199 | 0.048 |
| PowerSoil | 1.493 | 0.054 | 0.511 | 0.015 | 1.470 | 0.025 | 0.532 | 0.035 | 1.833 | 0.006 | 1.997 | 0.009 |
| New Technique | 1.845 | 0.007 | 1.249 | 0.161 | 1.870 | 0.003 | 1.721 | 0.288 | 1.860 | 0.011 | 1.360 | 0.083 |

*values in bold indicate best ratio

| | ZR Soil Microbe DNA | PureLink Microbiome DNA | PowerSoil DNA Isolation Kit | New Technique |
|---|---|---|---|---|
| O2 | 16.96 | 42.43 | 4.29 | 198.33 |
| O5 | 2.59 | 37.57 | 2.57 | 141.67 |
| Y2 | 163.67 | 139.67 | 100.63 | 268.67 |

The results show that the new technique according to the present disclosure produced the highest DNA yields of any kit. In particular, this new technique outperformed all the other kits when isolating DNA from old stool samples by over 400%.

Example 7

Inhibitor Removal from Soil Samples with Alternative Trivalent Metal Salts

This example tests other trivalent metal salts similar to aluminum ammonium sulfate dodecahydrate in removing inhibitors from soil samples.

All samples were done in duplicate and were pooled prior to inhibitor removal.

| | | 1 | 2 | 3 | 4 | 5 |
|---|---|---|---|---|---|---|
| Input | Soil sample (LCC), 0.25 g | x | x | x | x | x |
| Lysis | 1.2 g 0.1 mm + 1.2 g 0.5 mm ceramic beads (MOBIO) | x | x | x | x | x |
| | 1M NaSCN, 0.18M $Na_2HPO_4$, 800 µl | x | x | x | x | x |
| Inhibitor Removal | 3.75M $NH_4OAc$, 0.096M ErOAc, 200 µl | x | | | | |
| | 3.75M $NH_4OAc$, 0.096M $AlCl_3$, 200 µl | | x | | | |
| | 3.75M $NH_4OAc$, 0.096M $HoCl_3$, 200 µl | | | x | | |
| | 3.75M $NH_4OAc$, 0.096M $ErCl_3$, 200 µl | | | | x | |
| | 3.75M $NH_4OAc$, 0.096M AASD, 200 µl | | | | | x |

-continued

| | | 1 | 2 | 3 | 4 | 5 |
|---|---|---|---|---|---|---|
| DNA Bind | DNA binding solution I, 450 µl | x | x | x | x | x |
| DNA Wash | DNA wash solution I, 650 µl | x | x | x | x | x |
| | DNA wash solution II, 650 µl | x | x | x | x | x |
| DNA Elute | DNA elution solution, 100 µl | x | x | x | x | x |

LCC: soil sample form La Costa Canyon. This is a moderately high biomass soil of very high PCR inhibitor content.

The yields and purity of the isolated DNA are shown in the table below.

| Sample | (ng/uL) | Avg ng/uL | A260/ A280 | A260/ A230 | A260 | A280 | Nucleic Acid Factor | Baseline Correction (nm) | Baseline Absorbance |
|---|---|---|---|---|---|---|---|---|---|
| 1 | 60.252 | 63.596 | 1.894 | 1.928 | 1.205 | 0.636 | 50 | 340 | 0.092 |
| | 66.94 | | 1.877 | 1.822 | 1.339 | 0.713 | 50 | 340 | 0.054 |
| 2 | 64.607 | 66.1205 | 1.901 | 0.696 | 1.292 | 0.68 | 50 | 340 | 0.064 |
| | 67.634 | | 1.901 | 1.88 | 1.353 | 0.711 | 50 | 340 | 0.043 |
| 3 | 51.536 | 53.1475 | 1.92 | 1.984 | 1.031 | 0.537 | 50 | 340 | 0.112 |
| | 54.759 | | 1.886 | 0.683 | 1.095 | 0.581 | 50 | 340 | 0.083 |
| 4 | 55.92 | 57.314 | 1.883 | 2.086 | 1.118 | 0.594 | 50 | 340 | 0.079 |
| | 58.708 | | 1.901 | 1.586 | 1.174 | 0.618 | 50 | 340 | 0.049 |
| 5 | 67.559 | 70.1685 | 1.903 | 1.397 | 1.351 | 0.71 | 50 | 340 | 0.043 |
| | 72.778 | | 1.894 | 1.933 | 1.456 | 0.769 | 50 | 340 | 0.06 |

Figure 7:
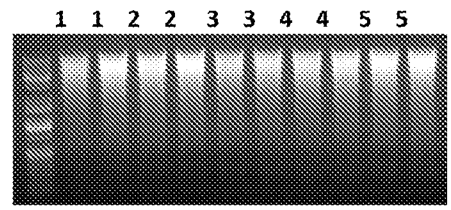
FIG. 7 shows gel electrophoresis of DNA isolated according to Example 7.

The gel electrophoresis of the isolated DNA is shown in FIG. 7.

PCR as set up below was used to quantify inhibition in isolated DNA.

| Inhibition PCR | | | | |
|---|---|---|---|---|
| volume/ rxn | volume | | final conc. | stock conc. |
| 4 | 96 µL | QuantiFast Pathogen Master Mix (5x) | 1 x | 5 x |
| 2 | 48 µL | Internal control assay | 1 x | 10 x |
| 7 | 168 µL | water | | |
| 2 | 48 µL | Internal control DNA (1200 copies) | | |
| 15 | 360 µL | | | |
| | rxns: | 24 | 15 µl Mix + 5 µl Sample | |

| No Template Control | | | | |
|---|---|---|---|---|
| volume/ rxn | volume | | final conc. | stock conc. |
| 4 | 12 µL | QuantiFast Pathogen Master Mix (5x) | 1 x | 5 x |
| 2 | 6 µL | Internal control assay | | |
| 9 | 27 µL | water | | |
| 15 | 45 µL | | | |
| | rxns: | 3 | 15 µl Mix + 5 µl water | |

PCR cycling was performed as follows: 95° C. for 5 minutes, and 45 cycles of 95° C. for 15 seconds and 60° C. for 30 seconds.

The results are shown in the table below.

| Results 5 µL | | | | | |
|---|---|---|---|---|---|
| Sample | ID | Ct | dCt | Avg dCt | stDev |
| 1 | PSP_76_1 | 29.72 | 1.95 | 2.0575 | 0.342381 |
| 2 | PSP_76_1 | 29.39 | 1.62 | | |
| 3 | PSP_76_1 | 30.11 | 2.34 | | |
| 4 | PSP_76_1 | 30.09 | 2.32 | | |
| 5 | PSP_76_2 | 28.91 | 1.14 | 1.1375 | 0.273542 |
| 6 | PSP_76_2 | 29.24 | 1.47 | | |
| 7 | PSP_76_2 | 28.91 | 1.14 | | |
| 8 | PSP_76_2 | 28.57 | 0.8 | | |
| 9 | PSP_76_3 | 29.88 | 2.11 | 1.905 | 0.147535 |
| 10 | PSP_76_3 | 29.53 | 1.76 | | |
| 11 | PSP_76_3 | 29.63 | 1.86 | | |
| 12 | PSP_76_3 | 29.66 | 1.89 | | |
| 13 | PSP_76_4 | 28.93 | 1.16 | 1.655 | 0.404351 |
| 14 | PSP_76_4 | 29.32 | 1.55 | | |
| 15 | PSP_76_4 | 29.56 | 1.79 | | |
| 16 | PSP_76_4 | 29.89 | 2.12 | | |
| 17 | PSP_76_5 | 32.46 | 4.69 | 4.72 | 0.167929 |
| 18 | PSP_76_5 | 32.34 | 4.57 | | |
| 19 | PSP_76_5 | 32.73 | 4.96 | | |
| 20 | PSP_76_5 | 32.43 | 4.66 | | |
| 21 | IC5 | 27.66 | | | |
| 22 | IC5 | 27.88 | | | |
| Avg IC5 | | 27.77 | | | |
| 25 | NTC | — | | | |
| 26 | NTC | — | | | |

The results show that all of the tested trivalent metal salts removed soil inhibitors more effectively than AASD with varying degrees of DNA loss. $AlCl_3$ (Test 2) removed the highest amount of inhibitors while removing the least amount of DNA.

Example 8

DNA and RNA Isolation from Soil Samples Using Different Lytic Reagents and Inhibitor Removal Solutions This example shows the effects of different lysis solutions and inhibitor removal on DNA and RNA isolation from soil samples.

Protocol:

add 0.25 g soil to bead tube, add 650 uL of lytic reagent II (tubes 1-4) OR 810 uL of lytic reagent I (tubes 5-7), add in 7 uL beta-ME and 100 uL of phenol (tubes 1-7), homogenize on vortex for 10 min on high, remove supernatant and place in new tube, and add 150 uL of 0.12M AASD (tubes 1-4) OR 250 uL of 3.75M $NH_4OAc$, 96 mM AASD (tubes 5-7), incubate 5 mins, spin, remove supernatant.

To Bind DNA:

add equal volume of DNA binding solution IV (tubes 1-4) OR equal volume of DNA binding solution I, and place 750 uL into spin column, centrifuge, keep flow through in separate 2 mL tube (i.e., the RNA flow through); repeat until all lysate is through the spin column.

To Bind RNA:

add equal volume of 100% ethanol (about 1 mL) to bind RNA in 5 mL tube, and place 750 uL into spin column, centrifuge; repeat until all lysate is through the spin column.

To Wash DNA/RNA:

wash spin columns with 650 µl of RNA wash solution, then wash spin column with 650 µl of ethanol (tubes 1-4) OR wash spin columns with 600 µl of DNA wash solution I, then wash spin column with 600 µl of DNA wash solution II, Spin dry for 2 min @ 10,000, and Add spin filter to a new tube and elute DNA/RNA in 100 uL $H_2O$ (tubes 1-7)

| | | 1 | 2 | 3 | 4 | 5 | 6 | 7 |
|---|---|---|---|---|---|---|---|---|
| input | backyard soil, 0.25 g | x | x | x | x | x | x | x |
| lysis | mixed ceramic beads (0.1 mm + 0.5 mm) | x | x | x | x | x | x | x |
| | Lytic reagent II, 650 uL | x | x | x | x | | | |
| | Lytic reagent I, | | | | | x | x | x |
| | phenol, 100 uL | x | x | x | x | x | x | x |
| | Beta-ME, 7 uL | x | x | x | x | x | x | x |
| Inhib-itor Removal | 0.12M AASD, 150 uL | x | x | x | x | | | |
| | 3.75M $NH_4OAc$, 96 mM AASD | | | | | x | x | x |
| DNA BIND | DNA binding solution IV, equal volume to lysate | x | x | x | x | | | |
| | DNA binding solution I, equal volume to lysate | | | | | x | x | x |
| RNA BIND | 100% ETOH, equal volume to lysate | x | x | x | x | x | x | x |

-continued

| | | 1 | 2 | 3 | 4 | 5 | 6 | 7 |
|---|---|---|---|---|---|---|---|---|
| DNA/ RNA WASH | RNA wash solution, 650 uL | x | x | x | x | | | |
| | DNA wash solution I, DNA wash solution II, 600 uL | | | | | x | x | x |
| DNA/ RNA ELUTE | RNase-free $H_2O$, 100 µL | x | x | x | x | x | x | x |

Figure 8:
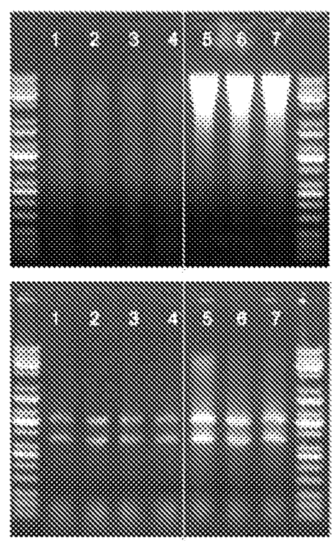
FIG. 8 shows gel electrophoresis of DNA (upper left) and RNA (lower left) and yields and purity of DNA (upper right) and RNA (lower right) isolated according to Example 8.

The results are shown in FIG. 8. Specifically, the upper left panel of FIG. 8 is the gel electrophoresis of isolated DNA; the lower left pane the gel electrophoresis of isolated RNA; the upper right table the yields and purity of the isolated DNA; and the lower right table the yields and purity of the isolated RNA.

The results show that the yields of DNA and RNA using lytic reagent I in combination with the inhibitor removal solution that comprises ammonium acetate and AASD were significantly higher than those using lytic reagent II in combination with AASD.

Example 9

Inhibitor Removal from Soil Samples with Aluminum Chloride

This example shows that aluminum chloride was effective in removing inhibitors from soil samples.

Samples 1 and 3 consisted of 5 replicates while samples 2 and 4 were done in duplicate.

| | | 1 × 5 | 2 | 3 × 5 | 4 |
|---|---|---|---|---|---|
| Input | VVG, 0.25 g | x | x | | |
| | LCC, 0.25 g | | | x | x |
| Lysis | 1.2 g 0.1 mm + 1.2 g 0.5 mm ceramic beads (MOBIO) | x | x | x | x |
| | 1M NaSCN, 0.18M $Na_2HPO_4$, 800 µl | x | x | x | x |
| Inhibitor Removal | 3.75M $NH_4OAc$, 0.096 M $AlCl_3$, 200 µl | x | | x | |
| | 3.75M $NH_4OAc$, 0.096M AASD, 200 µl | | x | | x |
| DNA Bind | DNA binding solution I, 450 µl | x | x | x | x |
| DNA Wash | DNA wash solution I, 650 µl | x | x | x | x |
| | DNA wash solution II, 650 µl | x | x | x | x |
| DNA Elute | DNA elution solution, 100 µl | x | x | x | x |

The yields and purity of the isolated DNA are shown in the tables below.

| Sample | (ng/uL) | Avg ng/uL | A260/ A280 | A260/ A230 | A260 | A280 | Nucleic Acid Factor | Baseline Correction (nm) | Baseline Absorbance |
|---|---|---|---|---|---|---|---|---|---|
| 1 | 47.626 | 46.948 | 1.837 | 1.575 | 0.953 | 0.518 | 50 | 340 | 0.064 |
| | 48.645 | | 1.853 | 1.909 | 0.973 | 0.525 | 50 | 340 | 0.094 |
| | 42.256 | | 1.808 | 0.685 | 0.845 | 0.468 | 50 | 340 | 0.056 |
| | 48.093 | | 1.852 | 1.975 | 0.962 | 0.519 | 50 | 340 | 0.077 |
| | 48.119 | | 1.862 | 1.1 | 0.962 | 0.517 | 50 | 340 | 0.09 |
| 2 | 44.363 | 45.839 | 1.893 | 1.595 | 0.887 | 0.469 | 50 | 340 | 0.085 |
| | 47.315 | | 1.82 | 1.569 | 0.946 | 0.52 | 50 | 340 | 0.096 |
| 3 | 62.457 | 65.074 | 1.883 | 1.795 | 1.249 | 0.664 | 50 | 340 | 0.112 |
| | 66.618 | | 1.877 | 1.574 | 1.332 | 0.71 | 50 | 340 | 0.064 |
| | 68.41 | | 1.904 | 0.884 | 1.368 | 0.718 | 50 | 340 | 0.073 |
| | 62.085 | | 1.892 | 1.932 | 1.242 | 0.656 | 50 | 340 | 0.063 |
| | 65.801 | | 1.91 | 1.953 | 1.316 | 0.689 | 50 | 340 | 0.067 |
| 4 | 62.29 | 63.510 | 1.895 | 1.799 | 1.246 | 0.657 | 50 | 340 | 0.077 |
| | 64.729 | | 1.886 | 0.588 | 1.295 | 0.687 | 50 | 340 | 0.087 |

| Sample | Concentration in the Qubit ug/mL | uL used | Dilu-tion | Sample Concentration ug/mL | Avg Concentration ug/mL |
|---|---|---|---|---|---|
| 1 | 2.57 | 10 | 20 | 51.4 | 52.1 |
| | 2.61 | 10 | 20 | 52.3 | |
| | 2.29 | 10 | 20 | 45.8 | |
| | 2.8 | 10 | 20 | 56 | |
| | 2.75 | 10 | 20 | 55 | |
| 2 | 2.72 | 10 | 20 | 54.3 | 56.6 |
| | 2.95 | 10 | 20 | 58.9 | |
| 3 | 3.73 | 10 | 20 | 74.6 | 78.56 |
| | 4.04 | 10 | 20 | 80.8 | |
| | 4.14 | 10 | 20 | 82.8 | |
| | 3.71 | 10 | 20 | 74.1 | |
| | 4.02 | 10 | 20 | 80.5 | |
| 4 | 3.88 | 10 | 20 | 77.6 | 79.2 |
| | 3.97 | 10 | 20 | 79.5 | |

Figure 9:
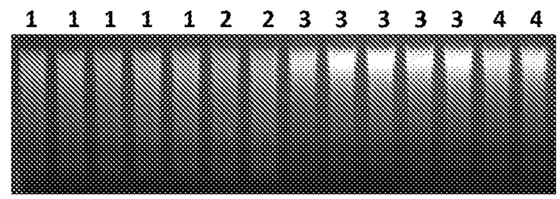
FIG. 9 shows gel electrophoresis of DNA isolated according to Example 9.

The gel electrophoresis of the isolated DNA is shown in FIG. 9.

PCR as set up below was used to quantify inhibition in isolated DNA.

| Inhibition PCR | | | | |
|---|---|---|---|---|
| volume/ rxn | volume | | final conc. | stock conc. |
| 4 | 128 μL | QuantiFast Pathogen Master Mix (5x) | 1 x | 5 x |
| 2 | 64 μL | Internal control assay | 1 x | 10 x |
| 7 | 224 μL | water | | |
| 2 | 64 μL | Internal control DNA (1200 copies) | | |
| 15 | 480 μL | | | |
| | rxns: | 32 | 15 μl Mix + 5 μl Sample | |

| No Template Control | | | | |
|---|---|---|---|---|
| volume/ rxn | volume | | final conc. | stock conc. |
| 4 | 12 μL | QuantiFast Pathogen Master Mix (5x) | 1 x | 5 x |
| 2 | 6 μL | Internal control assay | | |
| 9 | 27 μL | water | | |
| 15 | 45 μL | | | |
| | rxns: | 3 | 15 μl Mix + 5 μl water | |

PCR cycling was performed as follows: 95° C. for 5 minutes, and 45 cycles of 95° C. for 15 seconds and 60° C. for 30 seconds.

The results are shown in the table below.

| Sample | ID | Ct | dCt | Avg dCt | stDev |
|---|---|---|---|---|---|
| 1 | 77_1 | 29.12 | 1.24 | 1.041 | 0.407743 |
| 2 | 77_1 | 28.64 | 0.76 | | |
| 3 | 77_1 | 29.55 | 1.67 | | |
| 4 | 77_1 | 29.24 | 1.36 | | |
| 5 | 77_1 | 28.12 | 0.24 | | |
| 6 | 77_1 | 29.07 | 1.19 | | |
| 7 | 77_1 | 29.12 | 1.24 | | |
| 8 | 77_1 | 29.03 | 1.15 | | |
| 9 | 77_1 | 28.54 | 0.66 | | |
| 10 | 77_1 | 28.78 | 0.9 | | |
| 11 | 77_2 | 29.55 | 1.67 | 3.8 | 1.498332 |
| 12 | 77_2 | 31.79 | 3.91 | | |
| 13 | 77_2 | 32.96 | 5.08 | | |
| 14 | 77_2 | 32.42 | 4.54 | | |
| 15 | 77_3 | 27.86 | −0.02 | 0.48 | 0.288406 |
| 16 | 77_3 | 28.01 | 0.13 | | |
| 17 | 77_3 | 28.25 | 0.37 | | |
| 18 | 77_3 | 28.67 | 0.79 | | |
| 19 | 77_3 | 28.4 | 0.52 | | |
| 20 | 77_3 | 28.63 | 0.75 | | |
| 21 | 77_3 | 28.41 | 0.53 | | |
| 22 | 77_3 | 28.18 | 0.3 | | |
| 23 | 77_3 | 28.44 | 0.56 | | |
| 24 | 77_3 | 28.75 | 0.87 | | |
| 25 | 77_4 | 33.02 | 5.14 | 4.9875 | 0.621899 |
| 26 | 77_4 | 33.68 | 5.8 | | |
| 27 | 77_4 | 32.46 | 4.58 | | |
| 28 | 77_4 | 32.31 | 4.43 | | |
| 29 | IC5 | 27.87 | | | |
| 30 | IC5 | 27.89 | | | |
| Avg IC5 | | 27.88 | | | |
| 33 | NTC | — | | | |
| 34 | NTC | — | | | |

The results show that $AlCl_3$ produced DNA yields equal to the control (AASD) in both soil types. $AlCl_3$ reduced the dCt from 3.8 in VVG to 1 and from 5 to 0.5 in LCC, indicating $AlCl_3$ was more effective than AASD in removing PCR inhibitory compounds from both soil samples.

Example 10

Effects on Potassium Acetate and Ammonium Sulfate on DNA Isolation from Soil Samples This example examines the effects of potassium acetate and ammonium sulfate on DNA isolation from soil samples.

DNA isolation was performed as shown in the table below. All samples were done in duplicate.

| | D1a | D1b | D3a | 0 |
|---|---|---|---|---|
| Garden soil (VVG), 0.25 g | x | x | x | x |
| 0.7 mm garnet beads | x | x | x | x |
| Lysis solution I, 750 μl | x | x | x | x |
| Lysis solution II, 60 μl | x | x | x | x |
| 33.6 mM KOAc, 250 μl | x | | | |
| 33.6 mM KOAc, 3.8M $NH_4OAc$, 250 μl | | x | | |
| 3.8M Ammonium sulfate, 250 μl | | | x | |
| 3.8M Ammonium acetate, 250 μl | | | | x |
| 0.12M AASD, 200 μl | x | x | x | x |
| DNA binding solution II, 1200 μl | x | x | x | x |
| DNA wash solution I, 500 μl | x | x | x | x |
| DNA elution solution, 100 μl | x | x | x | x |

Figure 10:
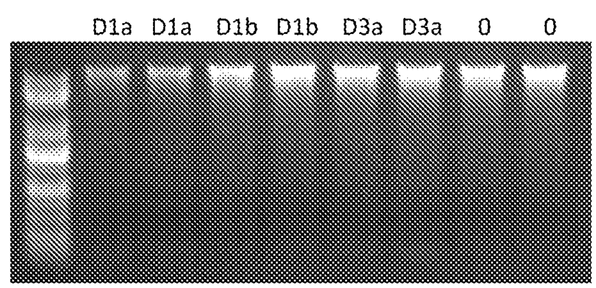
FIG. 10 shows gel electrophoresis of DNA isolated according to Example 10.

The gel electrophoresis of isolated DNA is shown in FIG. 10.

The yields and purity of isolated DNA as measured by NanoDrop are shown in the table below:

| Sample ID | ng/μl | A260 | A280 | 260/280 | 260/230 | Constant | Cursor Pos. | Cursor abs. | 340 raw |
|---|---|---|---|---|---|---|---|---|---|
| D1a | 12.01 | 0.24 | 0.133 | 1.81 | 1.24 | 50 | 230 | 0.194 | 0.042 |
| D1a | 14.72 | 0.294 | 0.165 | 1.79 | 1.26 | 50 | 230 | 0.233 | 0.054 |
| D1b | 22.87 | 0.457 | 0.258 | 1.77 | 1.38 | 50 | 230 | 0.332 | 0.031 |
| D1b | 25.68 | 0.514 | 0.276 | 1.86 | 1.48 | 50 | 230 | 0.347 | 0.037 |
| D3a | 25.11 | 0.502 | 0.267 | 1.88 | 1.26 | 50 | 230 | 0.4 | 0.033 |
| D3a | 24.41 | 0.488 | 0.256 | 1.91 | 1.87 | 50 | 230 | 0.261 | 0.034 |
| 0 | 25.38 | 0.508 | 0.282 | 1.8 | 1.5 | 50 | 230 | 0.338 | 0.021 |
| 0 | 24.62 | 0.492 | 0.263 | 1.87 | 1.63 | 50 | 230 | 0.303 | 0.032 |

The results show that the DNA yields and purity obtained by experiments D1b and D3a were similar to control experiment 0, while experiment D1a produced less DNA. Thus, ammonium sulfate had similar effects as ammonium acetate on DNA isolation from soil samples while potassium acetate produced less DNA than ammonium acetate.

Example 11

Effects on Sodium Acetate and Sodium Chloride on DNA Isolation from Soil Samples This example examines the effects of sodium acetate and sodium chloride on DNA isolation from soil samples.

DNA isolation was performed as shown in the table below. All samples were done in duplicate. All like samples (1-6) were pooled after bead beating. 550 μl was distributed to each collection tube.

| | | 1 | 2 | 3 | 4 | 5 | 6 | 7 |
|---|---|---|---|---|---|---|---|---|
| Input | Garden soil (VVG), 0.25 g | x | x | x | x | x | x | x |
| Lysis | Garnet bead tubes | x | x | x | x | x | x | x |
| | Lysis solution II, 60 μl | | | | | | | x |
| Inhibitor Removal | 1.87M NaOAc, 250 μl | x | | | | | | |
| | 3.75M NaOAc, 250 μl | | x | | | | | |
| | 7.5M NaOAc, 250 μl | | | x | | | | |
| | 3.75M NaCl, 250 μl | | | | x | | | |
| | 5M NaCl, 250 μl | | | | | x | | |
| | 3.8M $NH_4OAc$, 250 μl | | | | | | x | x |
| | 0.12M AASD, 200 μl | x | x | x | x | x | x | x |
| DNA Bind | DNA binding solution II, 1200 μl | x | x | x | x | x | x | x |
| DNA Wash | DNA wash solution I, 500 μl | x | x | x | x | x | x | x |
| DNA Elute | DNA elution solution, 100 μl | x | x | x | x | x | x | x |

Figure 11:
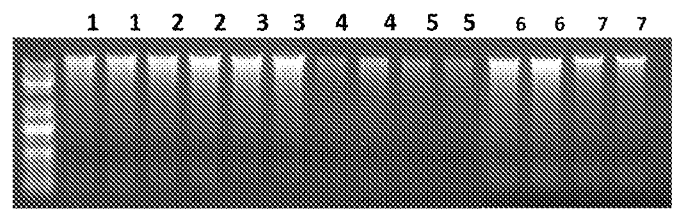
FIG. 11 shows gel electrophoresis of DNA isolated according to Example 11.

The gel electrophoresis of isolated DNA is shown in FIG. 11.

The yields and purity of isolated DNA as measured by NanoDrop are shown in the table below:

| Sample | (ng/uL) | A260/ A280 | A260/ A230 | A260 | A280 | Nucleic Acid Factor | Baseline Correction (nm) | Baseline Absorbance |
|---|---|---|---|---|---|---|---|---|
| 1 | 35.117 | 1.78 | 1.423 | 0.702 | 0.395 | 50 | 340 | 0.084 |
| 1 | 37.406 | 1.763 | 1.443 | 0.748 | 0.424 | 50 | 340 | 0.119 |
| 2 | 36.627 | 1.834 | 1.531 | 0.733 | 0.399 | 50 | 340 | 0.071 |
| 2 | 39.313 | 1.841 | 1.647 | 0.786 | 0.427 | 50 | 340 | 0.091 |
| 3 | 37.628 | 1.882 | 1.454 | 0.753 | 0.4 | 50 | 340 | 0.066 |
| 3 | 41.791 | 1.869 | 1.646 | 0.836 | 0.447 | 50 | 340 | 0.079 |
| 4 | 10.09 | 1.87 | 0.897 | 0.202 | 0.108 | 50 | 340 | 0.115 |
| 4 | 15.526 | 1.864 | 1.131 | 0.311 | 0.167 | 50 | 340 | 0.107 |
| 5 | 9.242 | 1.942 | 1.061 | 0.185 | 0.095 | 50 | 340 | 0.102 |
| 5 | 8.256 | 1.909 | 0.959 | 0.165 | 0.087 | 50 | 340 | 0.092 |
| 6 | 34.204 | 1.862 | 1.487 | 0.684 | 0.367 | 50 | 340 | 0.1 |
| 6 | 36.5 | 1.836 | 1.628 | 0.73 | 0.398 | 50 | 340 | 0.068 |
| 7 | 22.45 | 1.907 | 1.701 | 0.449 | 0.236 | 50 | 340 | 0.105 |
| 7 | 22.274 | 1.926 | 1.631 | 0.445 | 0.231 | 50 | 340 | 0.066 |

The results show that DNA yields using sodium acetate at the tested concentrations (experiments 1 to 3) were similar to those using ammonium acetate without including lysis solution II (experiment 6), while DNA yields using sodium chloride at the test concentrations (experiments 4 and 5) were lower than those using ammonium acetate without including lysis solution II (experiment 6). Comparing experiments 6 and 7 shows that including lysis solution II during DNA isolation reduced DNA yield.

Example 12

Effects on Cesium Acetate and Cesium Chloride on DNA Isolation from Soil Samples This example examines the effects of cesium acetate and cesium chloride on DNA isolation from soil samples.

DNA isolation was performed as shown in the table below. All samples were done in duplicate. All like samples (1-7) were pooled after bead beating. 550 µl was distributed to each collection tube.

| | | 1 | 2 | 3 | 4 | 5 | 6 | 7 | 8 |
|---|---|---|---|---|---|---|---|---|---|
| Input | Garden soil (VVG), 0.25 g | x | x | x | x | x | x | x | x |
| Lysis | Garnet bead tube | x | x | x | x | x | x | x | x |
| | Lysis solution II, 60 µl | | | | | | | | x |
| Inhibitor Removal | 1.87M CsOAc, 250 µl | x | | | | | | | |
| | 3.75M CsOAc, 250 µl | | x | | | | | | |
| | 7.5M CsOAc, 250 µl | | | x | | | | | |
| | 1.87M CsCl, 250 µl | | | | x | | | | |
| | 3.75M CsCl, 250 µl | | | | | x | | | |
| | 7.5M CsCl, 250 µl | | | | | | x | | |
| | 3.8M $NH_4OAc$, 250 µl | | | | | | | x | x |
| | 0.12M AASD, 200 µl | x | x | x | x | x | x | x | x |
| DNA Bind | DNA binding solution II, 1200 µl | x | x | x | x | x | x | x | x |
| DNA Wash | DNA wash solution I, 500 µl | x | x | x | x | x | x | x | x |
| DNA Elute | DNA elution solution, 100 µl | x | x | x | x | x | x | x | x |

Figure 12:
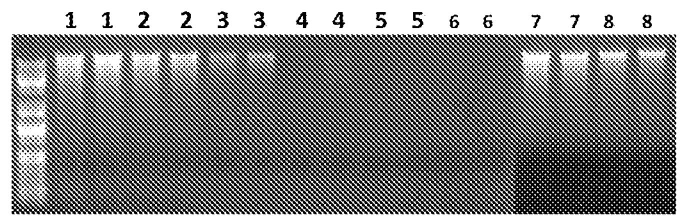
FIG. 12 shows gel electrophoresis of DNA isolated according to Example 12.

The gel electrophoresis of isolated DNA is shown in FIG. 12.

The yields and purity of isolated DNA as measured by NanoDrop are shown in the table below:

| Sample | (ng/uL) | A260/ A280 | A260/ A230 | A260 | A280 | Nucleic Acid Factor | Baseline Correction (nm) | Baseline Absorbance |
|---|---|---|---|---|---|---|---|---|
| 1 | 32.745 | 1.844 | 1.211 | 0.655 | 0.355 | 50 | 340 | 0.126 |
| 1 | 33.996 | 1.695 | 1.208 | 0.68 | 0.401 | 50 | 340 | 0.108 |
| 2 | 25.775 | 1.731 | 1.004 | 0.516 | 0.298 | 50 | 340 | 0.073 |
| 2 | 22.601 | 1.662 | 0.72 | 0.452 | 0.272 | 50 | 340 | 0.079 |
| 3 | 10.2 | 1.492 | 0.454 | 0.204 | 0.137 | 50 | 340 | 0.094 |
| 3 | 10.084 | 1.703 | 0.61 | 0.202 | 0.118 | 50 | 340 | 0.099 |
| 4 | 1.275 | 1.088 | 0.401 | 0.025 | 0.023 | 50 | 340 | 0.066 |
| 4 | 3.188 | 2.09 | 0.478 | 0.064 | 0.031 | 50 | 340 | 0.024 |
| 5 | 1.012 | 1.565 | 0.159 | 0.02 | 0.013 | 50 | 340 | 0.072 |
| 5 | 1.083 | 3.261 | 0.279 | 0.022 | 0.007 | 50 | 340 | 0.047 |
| 6 | 1.269 | 2.298 | 0.283 | 0.025 | 0.011 | 50 | 340 | 0.058 |
| 6 | 1.768 | 1.236 | 0.229 | 0.035 | 0.029 | 50 | 340 | 0.036 |
| 7 | 28.006 | 1.705 | 1.302 | 0.56 | 0.329 | 50 | 340 | 0.078 |
| 7 | 22.815 | 1.691 | 1.133 | 0.456 | 0.27 | 50 | 340 | 0.078 |
| 8 | 19.044 | 1.639 | 0.941 | 0.381 | 0.232 | 50 | 340 | 0.069 |
| 8 | 14.851 | 1.707 | 0.955 | 0.297 | 0.174 | 50 | 340 | 0.144 |

The results show that DNA yields decreased with increasing cesium acetate concentrations (experiments 1 to 3). Cesium acetate at the lowest concentration tested (experiment 1) produced higher DNA yields than the control using ammonium acetate but not lysis solution II (experiment 7). No DNA was isolated at any CsCl concentrations tested.

Example 13

Exemplary Method for Isolating DNA from Soil or Stool Samples

This example describes an exemplary method for isolating DNA from soil or stool samples according to the present disclosure.

Protocol in Summary

Soil or stool samples are lysed via chemical and mechanical homogenization. Lysis buffer is added to a mixed zirconium bead tube containing the sample. Bead beating can be carried out using a standard benchtop vortex with bead tube adapter or the high-powered TissueLyzer. Crude lysate is then subjected to a single-step precipitation reaction to remove PCR and RT-PCR inhibitory compounds. Following inhibitor removal, purified lysate is mixed with a DNA binding solution and passed through a silica spin filter membrane. The membrane is washed with a two-step washing regimen. Silica bound DNA is then eluted using a DNA elution buffer.

Detailed Protocol

Lysis:

1. Add up to 250 mg of soil (or stool) into a ytrrium-stabilized zirconium mixed bead tube (e.g., 0.1 and 0.5 mm beads, 1 gram of each).
2. Add 800 µl of lysis buffer (e.g., a buffer containing NaSCN and $Na_2HPO_4$).
3. Vortex on high to mix.
4. Bead beat on maximum speed for 10 minutes.
5. Centrifuge bead tube for 1 minute @ 15,000×g.
6. Transfer supernatant (expect 550 µl) to a new collection tube.

Inhibitor Removal:

7. Add 200 µl of inhibitor removal solution (e.g., a solution containing $NH_4OAc$ and $AlCl_3$).
8. Vortex on high to mix.
9. Centrifuge tube for 1 minute @ 15,000×g.
10. Transfer supernatant (expect 650 µl) to a new collection tube.

DNA Binding:

11. Add 450 μl of DNA binding solution I.
12. Vortex on high to mix.
13. Load 550 μl into spin column.
14. Centrifuge spin column for 1 minute @ 15,000×g. Discard flow through.
15. Load remaining lysate volume into spin column.
16. Centrifuge spin column for 1 minute @ 15,000×g. Discard flow through.

DNA Washing:

17. Add 650 μl of DNA wash solution I into spin column.
18. Centrifuge spin column for 1 minute @ 15,000×g. Discard flow through.
19. Add 500 μl of DNA wash solution II into spin column.
20. Centrifuge spin column for 1 minute @ 15,000×g. Discard flow through.
21. Centrifuge empty spin column for 2 minutes @ 15,000×g.
22. Transfer spin column to new collection tube.

DNA Elution:

23. Add 100 μl of DNA elution solution to the center of spin column membrane.
24. Centrifuge spin column for 1 minute @ 15,000×g. Discard spin column.

Example 14

Exemplary Method for Isolating DNA and RNA from Soil Samples

This example describes an exemplary method for isolating DNA and RNA from soil samples according to the present disclosure.

Protocol in Summary

Up to 250 mg of soil are lysed via chemical and mechanical homogenization. Lysis buffer is added to a mixed zirconium bead tube containing the sample. Bead beating can be carried out using a standard benchtop vortex with bead tube adapter or the high-powered TissueLyzer. Crude lysate is then subjected to a single-step precipitation reaction to remove PCR and RT-PCR inhibitory compounds. Following inhibitor removal, purified lysate is mixed with DNA binding solution and passed through a silica spin filter membrane. An equal volume of isopropanol is added to the DNA flow through and this solution is passed through a second spin column to capture total RNA. Both membranes are washed with a two-step washing regimen. Silica bound DNA and RNA are then eluted.

Detailed Protocol

Lysis:

1. Add up to 250 mg of soil into a ytrrium-stabilized zirconium mixed bead tube (e.g., 0.1 and 0.5 mm beads, 1 gram of each).
2. Add 800 μl of lysis buffer (e.g., a buffer containing NaSCN and Na2HPO4), 7 μl beta-mercaptoethanol and 100 μl phenol-chloroform-isoamyl alcohol (PIC), equilibrated with Tris buffer, pH 8.0.
3. Vortex on high to mix.
4. Bead beat on maximum speed for 10 minutes.
5. Centrifuge bead tube for 1 minute @ 15,000×g.
6. Transfer supernatant (expect 500 μl) to a new collection tube.

Inhibitor Removal:

7. Add 250 μl of inhibitor removal solution (e.g., a solution that contains NH4OAc and AlCl3).
8. Vortex on high to mix.
9. Centrifuge tube for 1 minute @ 15,000×g.
10. Transfer supernatant (expect 650 μl) to a new collection tube.

DNA Binding:

11. Add 450 μl of DNA binding solution I.
12. Vortex on high to mix.
13. Load 550 μl into spin column.
14. Centrifuge spin column for 1 minute @ 15,000×g. Retain flow-through, which contains RNA.
15. Load remaining lysate volume into spin column.
16. Centrifuge spin column for 1 minute @ 15,000×g. Retain flow through, which contains RNA
17. Place spin columns with immobilized DNA at +4° C. while RNA is being isolated.

RNA Binding:

18. Add 1000 μl of isopropanol to retained spin column flow-throughs from above.
19. Load 750 μl of RNA-containing lysate onto spin column.
20. Centrifuge spin column for 1 minute @ 15,000×g. Discard flow through.
21. Repeat lysate loading and centrifugation until all lysate has been processed through spin column.

DNA and RNA Washing:

22. Add 650 μl of DNA wash solution I onto spin column.
23. Centrifuge spin column for 1 minute @ 15,000×g. Discard flow through.
24. Add 650 μl of DNA wash solution 2 into spin column.
25. Centrifuge spin column for 1 minute @ 15,000×g. Discard flow through.
26. Centrifuge empty spin column for 2 minutes @ 15,000×g.
27. Transfer spin column to new collection tube.

DNA Elution:

28. Add 100 μl of DNA elution solution to the center of spin column membrane.
29. Centrifuge spin column for 1 minute @ 15,000×g. Discard spin column.

RNA Elution:

30. Add 100 μl of RNase-free water to the center of spin column membrane.
31. Centrifuge spin column for 1 minute @ 15,000×g. Discard spin column.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/662,063, filed Apr. 24, 2018, are incorporated herein by reference in their entirety except where incorporation of a reference or a portion thereof contradicts with the present disclosure. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for isolating nucleic acids from a sample, comprising:

(a) contacting a lysate of the sample or a supernatant of the lysate, or a portion of the lysate or the supernatant with one or more first agents selected from ammonium acetate, ammonium sulfate, potassium acetate, sodium acetate, sodium chloride, cesium acetate, and combinations thereof, and one or more second agents selected from aluminum chloride, erbium (III) acetate, erbium (III) chloride, holmium chloride, hafnium (IV) chloride, zirconium (IV) chloride, and combinations thereof to obtain a mixture, (b) separating the mixture of step (a) into a solid phase and a liquid phase, wherein the one or more second agents are primarily in the solid phase, and (c) isolating nucleic acids from the liquid phase of step (b).

2. The method of claim 1, wherein the first agent is ammonium acetate, and the second agent is aluminum chloride.

3. The method of claim 1, wherein the total concentration of the one or more first agents in the mixture of step (a) is 0.1 to 3M.

4. The method of claim 1, wherein the total concentration of the one or more second agents in the mixture of step (a) is in the range of 1 to 150 mM.

5. The method of claim 1, wherein nucleic acids isolated in step (c) comprise DNA, RNA or both.

6. The method of claim 1, wherein the sample is a stool sample, a plant sample, or an environmental sample.

7. The method of claim 1, wherein step (a) is performed by contacting the lysate of the sample or the supernatant of the lysate, or the portion of the lysate or the supernatant with a composition that comprises the one or more first agents and the one or more second agents.

8. The method of claim 1, wherein no precipitation, centrifugation or filtration has been performed between contacting the lysate of the sample or the supernatant of the lysate with the one or more first agents and contacting the lysate of the sample or the supernatant of the lysate with the one or more second agents.

9. The method of claim 1, wherein step (a) comprises:

(a) (1) contacting the lysate of the sample or the supernatant of the lysate with the one or more first agents to generate a mixture;

(a) (2) precipitating, centrifuging, or filtering the mixture of step (a) (1) to obtain a liquid phase; and (a) (3) contacting the liquid phase of (a) (2) with the one or more second agents.

10. The method of claim 1, wherein step (a) is performed in the presence of a lytic reagent.

11. The method of claim 10, wherein the lytic reagent comprises a chaotropic agent selected from sodium thiocyanate, sodium carbonate, ammonium thiocyanate, potassium thiocyanate, lithium thiocyanate, lithium perchlorate, guanidine sulfate, and combinations thereof.

12. The method of claim 10, wherein the lytic reagent further comprises one or more phosphates.

13. The method of claim 12, wherein the phosphate has one or more of the subsequent characteristics:

a) it is a phosphate dibasic, b) the cationic moiety in the phosphate is ammonium, sodium, potassium, or lithium, and/or c) it is sodium phosphate dibasic.

14. The method of claim 10, wherein the lytic reagent comprises sodium thiocyanate and sodium phosphate dibasic.

15. The method of claim 10, further comprising prior to step (a), contacting the sample or a portion of the sample with the lytic reagent to generate a lysate of the sample.

16. The method of claim 11, wherein the total concentration of the one or more chaotropic agents in the lytic reagent is in the range of 0.05 to 5M.

17. The method of claim 11, wherein the final concentration of the one or more chaotropic agents in total in the lysate is 0.01 to 4M.

18. The method of claim 12, wherein the total concentration of the one or more phosphates in the lytic reagent is 0.05 to 0.5M.

19. The method of claim 12, wherein the final concentration of the one or more phosphates in total in the lysate is 0.01 to 0.4M.

20. The method of claim 1, wherein the sample comprises a contaminant or inhibitor that forms a complex with the one or more second agents in step (a), and the complex is precipitated and removed from the liquid phase of step (b) by the one or more second agents.

21. The method of claim 1, further comprising:

(d) analyzing the nucleic acids isolated in step (c).

22. The method of claim 21, wherein step (d) comprises PCR, qPCR, RT-PCR, or nucleic acid sequencing.

23. The method of claim 1, wherein the amount of the sample in step (a) is less than 1 gram.

24. The method of claim 1, wherein the sample is a soil, water or air sample.

25. A kit for isolating nucleic acids from a sample, comprising:

(I) (a) a composition comprising:

(i) one or more first agents selected from ammonium acetate, ammonium sulfate, potassium acetate, sodium acetate, sodium chloride, cesium acetate, and combinations thereof, (ii) one or more second agents selected from aluminum chloride, erbium (III) acetate, erbium (III) chloride, holmium chloride, hafnium (IV) chloride, zirconium (IV) chloride, and combinations thereof, and (iii) optionally water;

OR (b) (i) one or more first agents selected from ammonium acetate, ammonium sulfate, potassium acetate, sodium acetate, sodium chloride, cesium acetate and combinations thereof, and (ii) one or more second agents selected from aluminum chloride, erbium (III) acetate, erbium (III) chloride, holmium chloride, hafnium (IV) chloride, zirconium (IV) chloride, and combinations thereof and (II) a nucleic acid-binding solid support.

26. A method for preparing a lysate from a sample, comprising:

(a) contacting a sample with a lytic reagent comprising one or more phosphates and one or more chaotropic agents selected from sodium thiocyanate, sodium carbonate, potassium thiocyanate, ammonium thiocyanate, lithium thiocyanate, lithium perchlorate, guanidine sulfate, and combinations thereof to generate a lysate, and (b) contacting the lysate, a supernatant of the lysate or a portion of the lysate or the supernatant of the lysate with one or more protein precipitating agents and one or more inhibitor removing agents, wherein the one or more inhibitor removing agents are selected from aluminum chloride, erbium (III) acetate, erbium (III) chloride, holmium chloride, hafnium (IV) chloride zirconium (IV) chloride, and combinations thereof.

27. The method of claim 26, wherein (i) the one or more inhibitor removing agents are selected from aluminum chloride, erbium (III) acetate, erbium (III) chloride and holmium chloride;

(ii) the inhibitor removing agent is aluminum chloride;

(iii) the one or more protein precipitating agents are selected from ammonium acetate, sodium acetate, cesium acetate, and a combination thereof, and the inhibitor removing agent is aluminum chloride;

(iv) the protein precipitating agent is ammonium acetate, and the inhibitor removing agent is aluminum chloride; or (v) the one or more protein precipitating agents are selected from ammonium acetate, ammonium sulfate, potassium acetate, sodium acetate, sodium chloride, cesium acetate, and combinations thereof.

28. The method of claim 26, wherein the method has one or more of the following characteristics:

(i) the lytic reagent comprises sodium phosphate dibasic and sodium thiocyanate;

(ii) the total concentration of the one or more phosphates in the lytic reagent is in the range of 0.05 to 0.5M;

(iii) the final concentration of the one or more phosphates in total in the lysate is in the range of 0.01 to 0.4M;

(iv) the total concentration of the one or more chaotropic agents in the lytic reagent is in the range of 0.05 to 5M;

(v) the total concentration of the one or more chaotropic agents in the lysate is in the range of 0.01 to 4M;

(vi) the sample is a stool sample, a plant sample, or an environmental sample;

(vii) the method further comprises mechanical disruption of the sample, optionally wherein the mechanical disruption is performed using high density beads; and/or (viii) the lytic reagent is used in combination with enzymatic lysis.

29. The method of claim 26, further comprising:

centrifuging the mixture of step (b) to obtain a supernatant from the mixture of step (b), and isolating nucleic acids from the supernatant of step (c).

30. A kit for preparing a lysate from a sample, comprising:

(I) (a) a lytic reagent comprising:

(1) one or more chaotropic agents selected from sodium thiocyanate, sodium carbonate, ammonium thiocyanate, potassium thiocyanate, lithium thiocyanate, lithium perchlorate, guanidine sulfate, and combinations thereof, and (2) one or more phosphates,

OR (b) (1) one or more chaotropic agents selected from sodium thiocyanate, sodium carbonate, ammonium thiocyanate, potassium thiocyanate, lithium thiocyanate, lithium perchlorate, guanidine sulfate, and combinations thereof, and (2) one or more phosphates, and (II) one or more second agents selected from aluminum chloride, erbium (III) acetate, erbium (III) chloride, holmium chloride, hafnium (IV) chloride, zirconium (IV) chloride, and (III) a nucleic acid-binding solid support.

31. The kit of claim 30, wherein the kit comprises (I) (a), and wherein the lytic reagent comprises sodium phosphate dibasic and sodium thiocyanate;

the lytic reagent is a solution, wherein the total concentration of the one or more chaotropic agents in the solution is in the range of 0.05 to 5M; and/or the lytic reagent is a solution, wherein the total concentration of the one or more phosphates in the solution is in the range of 0.05 to 0.5M.

32. The kit of claim 30, wherein the kit has one or more of the following characteristics:

(i) the one or more second agents are selected from aluminum chloride, erbium (III) acetate, erbium (III) chloride and holmium chloride;

(ii) the second agent is aluminum chloride;

(iii) the kit comprises one or more first agents that are selected from ammonium acetate, sodium acetate, cesium acetate, or a combination thereof and the second agent is aluminum chloride;

(iv) the kit comprises a first agent wherein the first agent is ammonium acetate, and the second agent is aluminum chloride; or (v) the kit comprises one or more first agents selected from ammonium acetate, ammonium sulfate, potassium acetate, sodium acetate, sodium chloride, cesium acetate, and combinations thereof.

33. The kit of claim 32, wherein the kit has characteristic (iii), (iv) or (v), and wherein the one or more first agents and the one or more second agents form a composition.

34. The kit of claim 33, wherein the composition is a solution.

35. The kit of claim 30, further comprising one or more of the following:

(i) high density beads suitable for mechanical disruption of the sample;

(ii) one or more of the solutions selected from a DNA binding solution, a DNA wash solution, a DNA elution solution, a RNA binding solution, a RNA wash solution, and a RNA elution solution;

(iii) a protein-binding solid phase; and/or (iv) one or more of a protein binding solution, a protein wash solution, and a protein elution solution.

36. The kit of claim 34, wherein the total concentration of the one or more first agents in the solution is in the range of 0.5 M to 10M, and/or wherein the total concentration of the one or more second agents in the solution is in the range of 0.01 M to 0.5 M.

* * * * *